US011254597B2

(12) United States Patent
Grison et al.

(10) Patent No.: US 11,254,597 B2
(45) Date of Patent: Feb. 22, 2022

(54) METHOD FOR THE PRODUCTION OF A MATERIAL OF PLANT ORIGIN THAT IS RICH IN PHENOLIC ACIDS, COMPRISING AT LEAST ONE METAL, FOR CARRYING OUT ORGANIC SYNTHESIS REACTIONS

(71) Applicant: CENTRE NATIONAL DE LA RECHERCHE SCIENTIFIQUE, Paris (FR)

(72) Inventors: Claude Grison, Castelnau le Lez (FR); David Carrasco, Viols le Fort (FR); Andrii Stanovych, Jacou (FR)

(73) Assignee: CENTRE NATIONAL DE LA RECHERCHE SCIENTIFIQUE, Paris (FR)

(*) Notice: Subject to any disclaimer, the term of this patent is extended or adjusted under 35 U.S.C. 154(b) by 215 days.

(21) Appl. No.: 16/498,912

(22) PCT Filed: Mar. 30, 2018

(86) PCT No.: PCT/EP2018/058362
§ 371 (c)(1),
(2) Date: Sep. 27, 2019

(87) PCT Pub. No.: WO2018/178374
PCT Pub. Date: Oct. 4, 2018

(65) Prior Publication Data
US 2020/0047165 A1 Feb. 13, 2020

(30) Foreign Application Priority Data

Mar. 31, 2017 (FR) .................................. 17 52822
Jan. 15, 2018 (FR) .................................. 18 00053

(51) Int. Cl.
C02F 9/00 (2006.01)
C07B 41/00 (2006.01)
B01J 23/34 (2006.01)
B01J 37/03 (2006.01)
B01J 37/12 (2006.01)
B09C 1/08 (2006.01)
C01G 45/02 (2006.01)
C07C 45/29 (2006.01)
C07C 45/51 (2006.01)
C07D 307/46 (2006.01)
C07D 307/48 (2006.01)
B01J 23/00 (2006.01)
B01J 23/02 (2006.01)
B01J 23/06 (2006.01)
B01J 23/10 (2006.01)
B01J 23/26 (2006.01)
B01J 23/40 (2006.01)
B01J 23/889 (2006.01)
B01J 35/02 (2006.01)
B01J 37/06 (2006.01)
B01J 37/08 (2006.01)
C02F 1/74 (2006.01)
(Continued)

(52) U.S. Cl.
CPC ............... C02F 9/00 (2013.01); B01J 23/002 (2013.01); B01J 23/007 (2013.01); B01J 23/02 (2013.01); B01J 23/06 (2013.01); B01J 23/10 (2013.01); B01J 23/26 (2013.01); B01J 23/34 (2013.01); B01J 23/40 (2013.01); B01J 23/8892 (2013.01); B01J 35/02 (2013.01); B01J 37/031 (2013.01); B01J 37/036 (2013.01); B01J 37/06 (2013.01); B01J 37/084 (2013.01); B01J 37/086 (2013.01); B01J 37/12 (2013.01); B09C 1/08 (2013.01); C01G 45/02 (2013.01); C02F 1/74 (2013.01); C07B 41/06 (2013.01); C07C 45/298 (2013.01); C07C 45/512 (2013.01); C07D 307/46 (2013.01); C07D 307/48 (2013.01); C02F 1/004 (2013.01); C02F 1/5245 (2013.01); C02F 1/66 (2013.01); C02F 1/722 (2013.01); C02F 2101/206 (2013.01)

(58) Field of Classification Search
CPC .................................. C02F 9/00; C07B 41/06
See application file for complete search history.

(56) References Cited

U.S. PATENT DOCUMENTS

2005/0217174 A1 10/2005 Angle et al.

FOREIGN PATENT DOCUMENTS

EP   0 333 218   9/1989
EP   1 806 177   7/2007
(Continued)

OTHER PUBLICATIONS

International Search Report, PCT/EP2018/058362, dated Jul. 30, 2018.
Guillaume Losfeld et al: "Design and performance of supported Lewis acid catalysts derived from metal contaminated biomass for FriedelCrafts alkylation and acylation", Catalysis Today, Elsevier, Amsterdam, NL, vo 1. 189, No. I, Feb. 21, 2012 (Feb. 21, 2012), pp. 111-116, XP028400049, ISSN: 0920-5861, DOI: 10.1016/J.CATTOD. 2012.02.044.

(Continued)

Primary Examiner — Sikarl A Witherspoon
(74) Attorney, Agent, or Firm — Nixon & Vanderhye

(57) ABSTRACT

Disclosed is a method for preparing a material of plant origin rich in phenolic acids, including at least one metal, including: preparing a material of plant origin chosen from: aquatic plants; materials rich in tannins; materials rich in lignin; and obtaining a material of plant origin, rich in phenolic acids, in which the ratio of the intensity of the vibration band of the C=O bond of the COOH group and the intensity of each of the vibration bands the aromatic ring determined in FT-IR is between 0.5 and 4. The material of plant origin is brought into contact with an effluent including from 0.1 to 1000 mg/l of at least one metal, thus obtaining a material of plant origin rich in phenolic acids including from 1 to 30% by weight of at least one metal relative to the total weight of the material.

20 Claims, No Drawings

(51) Int. Cl.
*C07B 41/06* (2006.01)
*C02F 1/00* (2006.01)
*C02F 1/52* (2006.01)
*C02F 1/66* (2006.01)
*C02F 1/72* (2006.01)
*C02F 101/20* (2006.01)

(56) References Cited

FOREIGN PATENT DOCUMENTS

| | | |
|---|---|---|
| EP | 2 554 256 | 2/2013 |
| WO | WO 2006/096472 | 9/2006 |
| WO | WO 2007/083304 | 7/2007 |
| WO | WO 2011/064462 | 6/2011 |
| WO | WO 2011/064487 | 6/2011 |
| WO | WO 2013/150197 | 10/2013 |
| WO | WO 2014/016509 | 1/2014 |
| WO | WO 2014/128283 | 8/2014 |
| WO | WO 2015/007990 | 1/2015 |
| WO | WO 2015/036714 | 3/2015 |
| WO | WO 2016/009116 | 1/2016 |
| WO | WO 2016/151261 | 9/2016 |
| WO | WO 2017/207947 | 12/2017 |

OTHER PUBLICATIONS

James R. Kastner et al: "Low Temperature Catalytic Oxidation of Hydrogen Sulfide and Methanethiol Using Wood and Coal Fly Ash" Environmental Science & Technology, vol. 37. No. 11. Jun. 1, 2003 (Jun. 1, 2003). pp. 2568-2574. XP055123527. ISSN: 0013-936X. DOI: 10.1021/es0259988 the whole document, table 1.

Kolar et al: "Low temperature catalytic oxidation of aldehydes using wood fly ash and molecular oxygen". Applied Catalysis B: Environmental, Elsevier. Amsterdam. NL, vol. 76. No. 3-4, Oct. 29, 2007 (Oct. 29, 2007). pp. 203-217. XP022318395. ISSN: 0926-3373 the whole document, table 1.

Kastner J R et al: "Catalytic ozonation of ammonia using biomass char and wood fly ash" Chemosphere. Pergamon Press. Oxford. GB, vol. 75. No. 6. May 1, 2009 (May 1, 2009) pp. 739-744. XP026035321. ISSN: 0045-6535. DOI: 10.1016/J.CHEMOSPHERE.2009.01.035.

Nour T Abdel-Ghani et al: "Biosorption for Metal Ions Removal From Aqueous Solutions: a Review of Recent Studies", International Journal of Latest Research in Science and Technology ISSN. vol. 3. No. 1. Jan. 1, 2014 (Jan. 1, 2014) pp. 2278-529924. XP055491348, the whole document.

French Search Report, FR 1752822, dated Jan. 19, 2018.

ately, or almost immediate, preparation of materials
METHOD FOR THE PRODUCTION OF A MATERIAL OF PLANT ORIGIN THAT IS RICH IN PHENOLIC ACIDS, COMPRISING AT LEAST ONE METAL, FOR CARRYING OUT ORGANIC SYNTHESIS REACTIONS The present invention relates to a method for preparing a material of plant origin rich in phenolic acids and comprising at least one metal.

The present invention also provides a method for the decontamination or treatment of an effluent comprising at least one metal by contacting a material of plant origin rich in phenolic acids with said effluent.

The present invention also relates to a method for carrying out an organic synthesis reaction using, as catalyst, said material of plant origin.

PRIOR ART

Human activities (quarrying, chemical, mining, metallurgical, agricultural activities, etc.) have led to the dispersion of metallic elements in aquatic systems. According to the Partenariat Francais pour l'Eau (PFE), "water is the first resource affected by climate change with all indicators at red". European Directive 2000/60/EC established a framework for improving water quality. This directive presents, in particular, a strategy for the control of pollution by substances of most concern. Metals are on the list of priority substances.

In addition, global mineral resources are becoming scarce. The development of green technologies and digital technology is putting a lot of pressure on demand. At the current rate of production, Sb, Zn, Pb will be exhausted within 20 years, Mn, Cu, Ni within 40 years. Rare earths and platinoids are only available in a very small number of countries.

OBJECTS OF THE INVENTION

Thus, there is a need to quickly and efficiently decontaminate waters polluted by metals.

There is also a need for a powerful method of ecological recycling of precious and rare precious metals, which are becoming increasingly scarce and whose supply is threatened.

Finally, there is a need to transform plant materials comprising at least one metal via a unique recovery method, phytocatalysis (or ecocatalysis) by producing new catalyst systems and in a position to replace advantageously conventional catalysts of chemistry.

Thus, the object of the invention is to provide a material and/or a method capable of solving one or more of the technical problems set forth in the present invention.

An object of the present invention is to solve the technical problem of providing a material and/or method for rapidly and efficiently decontaminating waters polluted by metals.

An object of the present invention is to solve the technical problem of providing a material and/or method for the environmentally friendly recycling of primary metals.

Another object of the present invention is to provide catalysts for carrying out organic synthesis reactions.

DETAILED DESCRIPTION OF THE INVENTION

The present invention relates to a method P1 for preparing a material of plant origin rich in phenolic acids, comprising at least one metal, said method comprising the following steps:

a. preparation of a material of plant origin from a dead plant preferably chosen from among:
   aquatic plants, preferably the roots of aquatic plants such as, for example, water hyacinth or water lettuce;
   materials rich in tannins such as, for example, coffee grounds or tea grounds;
   materials rich in lignin such as, for example, wheat straw, pine cones, pine bark, coconut wadding; and
   obtaining a material of plant origin, rich in phenolic acids, in which the ratio of the intensity of the vibration band of the C=O bond of the COOH group, and the intensity of each of the vibration bands of the aromatic ring determined in FT-IR, is between 0.5 and 4, preferably between 1 and 3.5, for example between 1 and 2.5;

b. bringing into contact the material of plant origin obtained at the end of step a) with an effluent comprising from 0.1 to 1000 mg/l of at least one metal, preferably for a duration of between 1 hour and 2 hours, at a temperature preferably between 10 and 30° C., and c. obtaining a material of plant origin rich in phenolic acids comprising from 1 to 30% by weight of at least one metal relative to the total weight of the material.

The roots of aquatic plants are advantageous in the method of the invention because of their polymeric structure. The aquatic plants advantageously used are water hyacinth (Eicchornia *crassipes*) or water lettuce (*Pistia stratiotes*).

For the purposes of the present invention, the term "material rich in tannins" means materials of plant origin consisting essentially of tannins. These materials include coffee grounds and green and/or black tea leaves.

For the purposes of the present invention, the term "materials rich in lignin" is intended to mean materials of plant origin mainly comprising lignin, such as cereal straw such as wheat straw, coconut or hemp fiber; fiber plants; the woods of deciduous trees such as birch, chestnut, *eucalyptus*; waste derived from wood, for example poplar, agave, pine sawdust, in particular pine bark, or sorghum, cones from conifers such as pine cones, husks such as chestnuts.

Surprisingly, it has been discovered that the materials of the invention are capable of solving one or more of the technical problems of the invention even though the plants from which they are obtained are no longer alive. Thus, according to a preferred variant of the invention, the material of plant origin comes from a dead plant, i.e. a plant that has been harvested, dried and optionally milled. For the purposes of the present invention, a dead plant is a plant which is not capable of reproducing, growing or having a physiological activity. Typically, the plants are harvested and left one or more days out of their culture medium prior to the preparation of a material of plant origin according to the present invention. This aspect is particularly advantageous in that it avoids the technical problem of growing plants for an immediate, or almost immediate, preparation of materials of plant origin according to the present invention.

According to a preferred variant of the invention, the plant from which is derived the material of plant origin used in the method of the invention has not been grown on an effluent comprising at least one metal, typically a polluted effluent.

Advantageously, in the method of the invention, the material of plant origin rich in phenolic acids is preferably a powder of roots of water hyacinths or water lettuce, preferably of water hyacinth, and preferably:

the powder is preferably derived from the ends of the roots;

the roots are devoid of aerial parts and/or the material has undergone dehydration prior to its implementation.

Preferably in the method of the invention, the material of plant origin is selected from water hyacinth, water lettuce, pine bark, and pine cones.

For the purposes of the present invention, a material of plant origin comprising phenolic acids is a material of plant origin that is insoluble in water and comprises an aromatic carbon skeleton and has at least carboxylic acid groups. These carboxylic acid groups may be naturally present in the material of plant origin, or derived from a chemical modification that makes it possible to enrich the carbon skeleton with carboxylic acid functions.

By "insoluble in water" is meant here a material of plant origin that can not be solubilized or dissolved in water. It necessarily forms a heterogeneous solid phase immiscible with water. For the purposes of the present invention, the term "insoluble" means that the limit of solubility in water of the material of plant origin is less than 1% by weight. Possibly, tiny parts are soluble (traces).

The presence of phenolic acids in the plant materials of the present invention may be determined by their infra-red analysis (FT-IR). The principle is based on the comparison of the intensities of the vibration bands of the aromatic ring and that of the C=O bond of the carboxylic acid unit.

The IR spectrum of the aromatic ring is characterized by three vibration bands between 1600 and 1400 $cm^{-1}$. The vibration band of the C=O bond of the COOH group is between 1680 and 1620 $cm^{-1}$, depending on the degree of conjugation.

By virtue of this infra-red analysis, it is possible to determine the ratio of the intensity of the vibration band of the C=O bond of the COOH group and the intensity of each of the vibration bands of the aromatic cycle.

Preferably, the infra-red analysis is performed with the FT-IR Spectrum 100 FT-IR spectrometer.

The infra-red data of certain materials of plant origin are grouped in the following Table 1. The value ΔT represents the difference of the transmittances T of two absorption bands, which makes it possible to quantify the intensities of these bands at the intensity of the incident signal. Transmittance is known to those skilled in the art.

With regard to water hyacinth roots and water lettuce roots, the intense and broad band at 1620 $cm^{-1}$ covers the aromatic band at 1600 $cm^{-1}$. In addition, the intensity of the band at 1620 is much higher than that of the strips at 1512 and 1414.

With regard to coffee and tea grounds, the intensity of the band at 1645 is much higher than that of the bands at 1525 $cm^{-1}$ and 1443-1414 $cm^{-1}$.

With regard to wheat straw, the intensity of the band at 1654 $cm^{-1}$ is lower than that of the strip at 1426 $cm^{-1}$, and with regard to the pine cone, the intensity of the band at 1658 $cm^{-1}$ is lower than that of the bands at 1602, 1510 and 1441-1419 $cm^{-1}$.

For each of these materials, it is possible to determine the ratio of the intensity of the vibration band of the C=O bond of the COOH group and the intensity of each of the vibration bands of the aromatic cycle, this ratio corresponding to the ratio of absorbances of the respective bands.

By "material of plant origin rich in phenolic acids" is meant, in particular, a material of plant origin characterized by a ratio of the intensity of the vibration band of the C=O bond of the COOH group and the intensity of each of the vibration bands of the aromatic ring greater than 1, preferably between 1 and 4, even more preferably between 1 and 3.5.

According to one variant, the ratio of the intensity of the vibration band of the C=O bond of the COOH group and the intensity of each of the vibration bands of the aromatic cycle is greater than 1.5.

It is preferred to select the maximum ratio value of the intensity of the vibration band of the C=O bond of the COOH group and the intensity of each of the vibration bands of the aromatic ring so that the material is insoluble. For certain materials, a certain solubility may appear by exceeding a value of this ratio of bands characterizing the phenolic acids. This maximum value of band ratio may be, for example, 3.5 or 3.

According to this definition, water hyacinth roots, water lettuce roots, coffee grounds and tea grounds are considered to be materials rich in phenolic acids. On the other hand,

TABLE 1

Infra-red data of different materials of plant origin

| Materials | IR data of the C=O band of the COOH group ($cm^{-1}$) | IR data of the aromatic cycle ($cm^{-1}$) | Ratio of the differences of the transmittances (ΔT) between the functional groups C=O/Ar |
|---|---|---|---|
| Roots of water hyacinths | 1620 (ΔT = 8.6%) | 1512 (ΔT = 3.0%) | 2.9 |
|  |  | 1414 (ΔT = 5.1%) | 1.7 |
| Roots of water lettuce | 1626 (ΔT = 11.5%) | 1513 (ΔT = 8.8%) | 1.3 |
|  |  | 1416 (ΔT = 10.7%) | 1.1 |
| Coffee grounds | 1645 (ΔT = 8.2%) | 1525 (ΔT = 5.6%) | 1.5 |
|  |  | 1443-1414 (ΔT = 7.3%) | 1.1 |
| Tea grounds | 1626 (ΔT = 7.2%) | 1517 (ΔT = 5.5%) | 1.3 |
|  |  | 1455 (ΔT = 6.4%) | 1.1 |
| Wheat straw | 1654 (ΔT = 2.9%) | 1598 (ΔT = 2.8%) | 1 |
|  |  | 1510 (ΔT = 2.8%) | 1 |
|  |  | 1426 (ΔT = 3.5%) | 0.8 |
| Pine cones | 1658 (ΔT = 4.6%) | 1602 (ΔT = 5.6%) | 0.8 |
|  |  | 1510 (ΔT = 5.6%) | 0.8 |
|  |  | 1441-1419 (ΔT = 6.2%) | 0.7 | wheat straw and pine cone are not considered as materials rich in phenolic acids and will be advantageous only after functionalization.

Moreover, for the purpose of the present invention, the term "material rich in phenolic acids" also means a material of plant origin comprising phenolic acid functions and capable of fixing more than 90%, preferably more than 95%, preferably more than 99%, advantageously 100% by weight of at least one metal included in an effluent, for example said effluent comprising from 0.1 to 1000 mg/L of at least one metal. For the purposes of the present invention, "fixing" is understood to mean a complexing reaction between the phenolic acids included in the material of plant origin and the metals with which it is in contact. Advantageously, the material of plant origin rich in phenolic acids is capable of fixing more than 90%, preferably more than 95%, preferably more than 99% by weight of at least one metal in ionic form included in an effluent, wherein, for example, said effluent comprises from 0.1 to 1000 mg/L of at least one metal.

The expression "a metal in ionic form" is understood to mean a metal in the form of M(I), M(II), M(III), M(IV), M(V) or M(VI). Preferably, the metal is in cationic form.

It is also understood that the ionic metal adsorption or fixing capacity of the material of plant origin and thus the percentage of decontamination generally depends both on the mass of said material brought into contact with the medium containing the metals in ionic forms and the quantity by weight of the metals in ionic forms contained in the medium to be decontaminated. For the purpose of the present invention, the term "absorption capacity" means the ability of the material of plant origin to fix the metals on its surface. By "surface" is meant the inner and outer surface of the material. The absorption capacity may be expressed in mmol of metal per gram of sorbent, or in gram of metal per gram of sorbent.

The inventors of the present application have discovered that the fact that the materials of plant origin can fix the metals included in an effluent was very probably due to the presence of natural or functionalized phenolic acids in these materials. We talk about biosorption. We also speak of biosorbent for the material of plant origin according to the invention.

For the purpose of the present invention, the term "biosorption" is intended to mean the non-physiological physico-chemical method by which the phenolic-rich plant materials of the present invention adsorb certain metals. The biosorption takes place during the bringing into contact step b) of the method of the invention.

By "preparation of a material of plant origin" is meant any necessary step to obtain a material of plant origin, such as a dehydration step and/or a grinding step.

Typically, a method P1 according to the present invention comprises, in step a) for the preparation of the material of plant origin, a step of dehydration and optionally grinding of the plant from which the material is obtained.

By dehydration is meant a treatment of the vegetable material preferably at a temperature between 20° C. and 90° C., preferably in air.

The grinding step may be carried out for a few minutes using a blender. This step makes it possible to obtain a ground material of plant origin, preferably in the form of a powder, preferably in the form of a powder whose particle size is less than 1.5 mm, and, for example, between 0.5 and 1.5 mm. The particle size is preferably measured through a sieve with 1.5 mm mesh openings. Thus, the particle size represents the maximum size of the powder grains of the material of plant origin. Grinding may be used for all materials of plant origin. Advantageously, the coffee and tea grounds do not undergo a grinding stage. However, they are thoroughly washed with hot water until the soluble products they contain are eliminated.

Following the grinding step, the powder obtained can be washed with water, preferably between 25 and 50° C., then this powder is filtered, preferably on cellulose, and dried at a temperature between 40 and 90° C., for example in an oven at 80° C. for 12 h.

The materials rich in tannin are washed, filtered and dried under the same conditions as those described above.

The materials rich in lignin are first washed preferably with isopropanol to remove the resin acids. They are then ground for a few minutes using a blender. The powder obtained is washed again preferably with isopropanol, then with hot water, filtered on cellulose, before being dried in an oven at 80° C. for 12 h. Preferably, the material of plant origin used in step a) of the invention is free or substantially free of metals selected from the group of platinoids and in particular Pt, Pd or Rh, rare earths and in particular Ce, Eu, Yb and Sc; or from the group comprising Zn, Mn, Ni, Cu, Fe, Al, Ca, Mg, As, Sb, Cr, Cd, Ni and Co, preferably from the group comprising Zn, Mn, Ni, Cu, Fe, Al, Ca, Mg, As, Cd, Ni and Co.

Advantageously, each content of Fe, Al, Cu, Ni, Zn and Mn in the material of plant origin used in step a) of the invention is less than 0.01% by weight.

Typically, the material of plant origin used in step a) of the invention comprises at least one physiological metal selected from Ca, K, Mg or Na. Preferably, the material of plant origin used in step a) of the invention comprises from 0.1 to 3.5% by weight of at least one metal chosen from Ca, K, Mg or Na.

Advantageously, the material may comprise from 0.8 to 3.4% by weight of Ca, from 0.1 to 0.8% by weight of K, from 0 to 0.5% by weight of Mg, and from 0 to 0.7% by weight of Na. Preferably, the water hyacinth roots comprise 3.4% by weight of Ca, 0.8% by weight of K, 0.5% by weight of Mg, and 0.7% by weight of Na; the coffee grounds comprise 0.5% by weight of Ca, 0.8% by weight of K, 0.2% by weight of Mg; the pine cone comprises 0.5% by weight of CA and 0.2% by weight of K; and pine bark comprises 0.8 wt % Ca and 0.1 wt % K.

During the step b) of bringing into contact the material of plant origin obtained at the end of step a) with an effluent comprising from 0.1 to 1000 mg/l, preferably from 5 to 100 mg/l, preferably 14 to 40 mg/l of at least one metal; the material of plant origin, which is then preferably in the form of a powder insoluble in water, is added to an effluent comprising from 0.1 to 1000 mg/l, preferably from 5 to 100 mg/l, preferably from 14 to 40 mg/l of at least one metal. The material is added in an amount sufficient to bind said at least one metal in ionic form. This quantity is determined by studying the absorption capacity of each material of plant origin. The step b) of bringing into contact may be carried out by any means known to those skilled in the art, for example via the elution of the effluent in a column comprising the material of plant origin. The material of plant origin may initially comprise physiological metals (Ca, Na, K) and releases them when placed in contact with the effluent (step b). The system is similar to an ion exchange resin: Na and K are replaced by Fe and Mn.

For the purposes of the present invention, the term "effluent" means an aqueous liquid medium, which may, for example, be chosen from:
  a reaction medium in which a chemical reaction involving
    a metal catalyst has been carried out; or an effluent from a reaction medium in which a chemical reaction involving a metal catalyst has been carried out; or an effluent of extractive or industrial origin, for example originating from mines, quarries or the steel industry and comprising metallic elements.

The metals present in the effluents may be divided into three categories:

The strategic resources: platinoids (Pd, Pt, Rh, . . . ) and rare earths (Ce, Eu, Yb, Sc, . . . );

The primary resources: Zn, Mn, Ni, Cu, Fe, Al, Ca, Mg;

Toxic elements: As, Sb, Cr, Cd, Pb, Ni, Co.

Preferably, the effluent comprises at least one metal selected from the group of platinoids and, in particular, Pt, Pd or Rh, rare earths and, in particular, Ce, Eu, Yb and Sc; or from the group comprising Zn, Mn, Ni, Cu, Fe, Al, Ca, Mg, As, Sb, Cr, Cd, Ni and Co, preferably from the group comprising Zn, Mn, Ni, Cu, Fe, Al, Ca, Mg, As, Cd, Ni and Co. Advantageously, the effluent comprises a metal selected from the group comprising Cu, Pb, Cd or Ni or from the group comprising Pd, Sc, Co, Fe, Mn, As, Ce, Eu, Yb.

Advantageously, the effluent comprises at least one metal in ionic form chosen from scandium (Sc), manganese (Mn), iron (Fe), cobalt (Co), nickel (Ni), copper (Cu), lead (Pb), zinc (Zn), ruthenium (Ru), palladium (Pd), cadmium (Cd), iridium (Ir), rhodium (Rh), platinum (Pt), lithium (Li), osmium (Os), mercury (Hg), arsenic (As), antimony (Sb), chromium (Cr), aluminum (Al) or a metal of the series of lanthanides including europium (Eu), ytterbium (Yb), cerium (Ce).

Advantageously according to the invention, the effluent is an effluent of extractive or industrial origin comprising metallic elements and, in particular, an effluent coming from a quarry and comprising at least one metal chosen from iron (Fe), manganese (Mn), zinc (Zn), nickel (Ni), copper (Cu), lead (Pb), scandium (Sc), cerium (Ce) and lithium (Li), or osmium (Os).

Alternatively, the effluent may comprise one or more metals selected from Pb, Sc, Eu, and Ce, or from the rare earths, or from Co and Fe, Mn, or from Cr, Zn Ni, As, Cd or Cu.

Advantageously, step b) of the method of the invention takes place for a period sufficient to fix a satisfactory amount of metal by the material of plant origin, and typically takes place for at least one hour, preferably at least one two hours, or for a period of between 1 and 2 hours. Preferably, the temperature of this step is greater than 0° C. preferably between 10° C. and 30° C., preferably between 20° C. and 25° C.

Following this step b), the medium comprising the effluent and the material of plant origin may be filtered to recover the material of plant origin comprising at least one metal. Advantageously, the material of plant origin fixes at least 90%, preferably more than 95%, preferably more than 99% by weight, preferably substantially 100% of said metal present in the effluent. This filtration may be performed in "batch" or column mode. By "substantially" is meant here that the metal remains in the effluent is in trace form.

Advantageously according to the method of the invention,
when the material of plant origin is water hyacinth, the effluent comprises at least one metal selected from Sc, Ni, Ce, Yb, Co, Ni, Cu, Pd, Pt, Rh, Mn, Fe, Zn, As, Cr or Sb, preferably from Sc, Ni, Ce, Yb, Co, Ni, Cu, Pd, Pt, Mn, Fe, Zn or As;

when the material of plant origin is water lettuce, the effluent comprises at least one metal chosen from Pd, Pt, Rh or Ni, preferably from Pd, Pt or Ni;

when the material of plant origin is coffee grounds, the effluent comprises at least one metal chosen from Pd, Pt, Rh, Mn, Fe, Zn, Ni or Cd, preferably from Pd, Pt, Mn, Fe, Zn, Ni or Cd.

Advantageously, at the end of step b), the material of plant origin is dried in an oven, preferably at a temperature between 70° C. and 90° C., preferably at 85° C., and then it is heat treated, for example, at 550° C. for 6 hours.

Preferably, the material of plant origin obtained in step c) comprises at least one metal selected from the group of platinoids and, in particular, Pt, Pd or Rh, rare earths and, in particular, Ce, Eu, Yb and Sc; or from the group consisting of Zn, Mn, Ni, Cu, Fe, Al, Ca, Mg, As, Sb, Cr, Cd, Ni and Co; advantageously chosen from the group comprising Cu, Pb, Cd or Ni or from the group comprising Pd, Sc, Co, Fe, Mn, As, Ce, Eu, Yb.

Advantageously, the material obtained according to the method of the invention comprises from 1 to 20% by weight, for example from 1 to 10% by weight, of metals selected from Sc, Ni, Ce, Yb, Co, Ni, Cu, Pd, Pt, Mn, Fe, Zn, As or Cd.

Preferably, the metal content in the material of plant origin obtained in step c) is determined by MP-AES (Microwave Plasma Atomic Emission Spectrometry) or ICP-MS (Inductively Coupled Plasma Mass Spectroscopy). This metal content may be measured directly after the drying and the heat treatment carried out before step c). The metal content is expressed as a function of the total weight of material of plant origin obtained at the end of step b).

The invention also relates to a method P2 for the decontamination or treatment of an effluent comprising at least one metal, said method comprising the following steps:
a. preparation of a material of plant origin from a dead plant chosen from:
  aquatic plants, preferably the roots of aquatic plants such as water hyacinth or water lettuce;
  materials rich in tannins such as coffee grounds or tea grounds;
  materials rich in lignin such as wheat straw, pine bark, pine cones, coconut husks; and
  obtaining a material of plant origin, rich in phenolic acids, in which the ratio of the intensity of the vibration band of the C=O bond of the COOH group and of each of the vibration bands of the aromatic cycle determined in FT-IR is between 0.5 and 4, preferably between 1 and 3.5, for example between 1 and 2.5;
b. bringing into contact the material of plant origin obtained at the end of step a) with an effluent comprising from 0.1 to 1000 mg/l of at least one metal, preferably for a duration of between 1 hour and 2 hours, at a temperature preferably between 10 and 30° C., and
c. obtaining an effluent comprising less than 100 mg/l by weight of said at least one metal.

The decontamination method of the invention advantageously makes it possible to meet environmental discharge standards and may be chemoselective.

All the embodiments, variants and preferred features of the method P1 apply, alone or in any of their combinations, as well as to the method P2 for decontamination according to the invention.

Advantageously, the sufficient amount of material of plant origin is from 0.5 g to 20 g/l for the decontamination of industrial effluents containing metal concentrations in ionic form of 5 to 500 mg/l. This is particularly true when the metal is selected from scandium (Sc), manganese (Mn), iron (Fe), cobalt (Co), nickel (Ni), copper (Cu), lead (Pb)), zinc (Zn), ruthenium (Ru), palladium (Pd), cadmium (Cd), iridium (Ir), rhodium (Rh), platinum (Pt), lithium (Li), osmium (Os), mercury (Hg), arsenic (As), antimony (Sb), chromium (Cr), aluminum (Al) or a metal of the lanthanide series, especially I europium (Eu), ytterbium (Yb), cerium (Ce).

Preferably, step c) of the method P2 makes it possible to obtain an effluent comprising from 0 to 100 mg/l, preferably from 0 to 50 mg/l, advantageously from 0 to 15 mg/l, more advantageously from 0 to at 5 mg/l in at least one metal selected from Sc, Ni, Ce, Yb, Co, Ni, Cu, Pd, Pt, Mn, Fe, Zn, As or Cd.

According to one particular embodiment, the material of plant origin which has been prepared at the end of step a) in the methods P1 or P2 of the invention is characterized by a ratio of the intensity of the band of vibration of the C=O bond of the COOH group and the intensity of each of the aromatic ring vibration bands determined in FT-IR of less than 1, preferably between 0 and 1.

In this case, the methods P1 or P2 may comprise a step of functionalization of the material of plant origin obtained at the end of step a), said step being prior to step b), and obtaining a material of plant origin in which the ratio of the intensity of the vibration band of the C=O bond of the COOH group and the intensity of each of the aromatic ring vibration bands determined in FT-IR, is greater than 1, preferably between 1 and 3, even more preferably between 1 and 2.5. Pine cones and pine bark are characterized by a ratio of the vibration band intensity of the C=O bond of the COOH group and the intensity of each of the aromatic ring vibration bands determined in FT-IR less than 1, but the functionalization step is not necessary for these materials which complex palladium.

When the methods P1 or P2 according to the invention comprise a functionalization step, this may be carried out for example via:
  a carboxylation reaction of the material of plant origin obtained at the end of step a) with a carboxylic acid anhydride in an aprotic polar solvent such as ethyl acetate, the anhydride being preferably chosen among mixed anhydrides, cyclic, aliphatic, functionalized, generated in situ or prior to the implementation of the carboxylation reaction; or
  an autocatalysed esterification reaction between the material of plant origin obtained at the end of step a) and a polyacid, this reaction taking place in a solvent preferably chosen from ethanol or ethyl acetate; or
  an esterification reaction followed by hydrolysis and transfunctionalization.

Advantageously, the functionalization step may be carried out via the opening of functionalized or non-functional anhydrides, generated in situ or prepared beforehand, such that glutaric anhydride, preferably cyclic carboxylic anhydrides with five centers, preferably succinic anhydride and itaconic anhydrides, with a polyacid by autocatalysis, preferably citric acid, succinic acid, maleic acid or glutaric acid introduced in a non-aqueous medium, preferably aprotic, such as ethyl acetate.

The present invention also relates to a material of plant origin, rich in phenolic acids, optionally comprising at least one metal, said material being capable of being obtained according to the method P1 or P2 of the invention, and optionally comprising functionalized phenolic acid functions.

The present invention also relates to a material of plant origin, rich in phenolic acids, optionally comprising at least one metal, characterized in that said plant origin is chosen from:
  aquatic plants, preferably the roots of aquatic plants such as water hyacinth or water lettuce;
  materials rich in tannins such as coffee grounds or tea grounds;
  materials rich in lignin such as wheat straw, pine cones, pine bark, coconut husks, said material having a ratio of the intensity of the vibration band of the C=O bond of the COOH group and the intensity of each of the aromatic ring vibration bands determined in FT-IR is greater than 1, preferably comprised between 1 and 3, and optionally comprising functionalized phenolic acid functional groups.

Advantageously, the material of plant origin according to the invention is characterized by a degree of functionalization of between 0.0007 and 0.0014 $mol_{NaOH}$/g of material in the case of water hyacinth and between 0.0006 and 0,0018 $mol_{NaOH}$/g of material in the case of coffee grounds. This degree of functionalization may be measured by titration of the functionalized material with a solution of NaOH (2M) until a pH of 7 is obtained.

The inventors of the present application have surprisingly shown that the use of plant materials ground and packaged in powder form, for example, a powder of the roots of aquatic plants, especially water hyacinth, can fix metals chosen, in particular, from scandium (Sc), manganese (Mn), iron (Fe), cobalt (Co), nickel (Ni), copper (Cu), lead (Pb), zinc (Zn), ruthenium (Ru), palladium (Pd), cadmium (Cd), iridium (Ir), rhodium (Rh), platinum (Pt), lithium (Li), osmium (Os), mercury (Hg), arsenic (As), antimony (Sb), chromium (Cr), aluminum (Al) or a metal of the lanthanide series, in particular europium (Eu), ytterbium (Yb), cerium (Ce), more effectively compared with the use of living plants fixing the metals by rhizofiltration.

Materials of plant origin comprising at least one metal and obtained by the methods of the invention, and thus having fixed at least one metal in ionic form chosen, in particular, from scandium (Sc), manganese (Mn), iron (Fe), cobalt (Co), nickel (Ni), copper (Cu), lead (Pb), zinc (Zn), ruthenium (Ru), palladium (Pd), cadmium (Cd), iridium (Ir), rhodium (Rh), platinum (Pt), lithium (Li), osmium (Os), mercury (Hg), arsenic (As), antimony (Sb), chromium (Cr), aluminum (Al) or a metal of the lanthanide series, in particular europium (Eu), ytterbium (Yb), cerium (Ce), may be directly recovered by ecocatalysis.

The invention also relates to a method P3 for preparing an organic synthesis reaction catalyst comprising heat treatment of a material of plant origin comprising at least one metal according to the invention or obtainable according to one of the following: any of the methods of the invention, preferably at a temperature between 500 and 800° C. and preferably for a period of between 2 and 8 hours, and obtaining a calcined material.

The present invention also relates to a material of plant origin comprising at least one metal, or obtainable according to the methods of the invention. Advantageously, the material of plant origin comprising at least one metal or capable of being obtained according to the methods of the invention comprises the mixed salt: $Ca_2Mn_3O_8$.

All the embodiments, variants, and preferred characteristics of the methods P1 and P2 apply, alone or in any of their combinations, as wel as to the method P3.

For the purposes of the present invention, the heat treatment is carried out in air or under an argon atmosphere in an oven preferably for a period of between 4 and 6 hours. The heat treatment may also be carried out in two steps, the first at a temperature below 500° C., preferably of the order of 350° C., and in a second step at a temperature of the order of 550° C., each step being performed for about 3 hours.

Preferably, the heat treatment is carried out at 550° C. for 6 hours.

Preferably, the method P3 comprises acid treatment of the calcined material. Preferably, the acid treatment is carried out with hydrochloric acid, in particular hydrochloric acid at a concentration of between 0.1N and 12N, or formic acid, sulfuric acid and hydrobromic acid, trifluoroacetic acid or trifluoromethanesulphonic acid.

The calcined materials may be activated and used in chemical catalysis for the synthesis of biomolecules with high added value. Opportunities derived from the new type of biomass proposed are numerous and give rise to a considerable number of possibilities in acid catalysis, green oxidation, oxidation-reduction reactions, and couplings, and, in particular, in the homogeneous phase.

Thus, the invention relates to a method P4 for carrying out an organic synthesis reaction involving the calcined material as a catalyst.

Advantageously, the method P4 comprises the following steps:
the heat treatment of a material of plant origin comprising at least one metal according to the invention or obtainable according to any one of the methods of the invention, preferably at a temperature of between 500 and 800° C., and preferably for a period of between 2 and 8 hours, and obtaining a calcined material;
the implementation of an organic synthesis reaction involving the calcined material as a catalyst.

All the embodiments, variants and preferred characteristics of the methods P1, P2 and P3 apply, alone or in any of their combinations, as well as to the method P4.

Advantageously, in the method P4, the implementation of an organic synthesis reaction of the invention is carried out without addition of metal from an origin other than the calcined material.

According to the present invention, the term "catalyst" means the product obtained following the method P3.

The present application also relates to the use as a catalyst, and, in particular, in a homogeneous phase, of a composition containing a metal catalyst resulting, optionally after acid treatment, from ash obtained by heat treatment of a material of plant origin, in the form of a powder insoluble in water in sufficient quantity to fix at least 90%, 95% or preferably 100% of the metal(s) present in the liquid medium to be treated and which is rich in phenolic acids, having fixed at least one metal in ionic form chosen, in particular, from scandium (Sc), manganese (Mn), iron (Fe), cobalt (Co), nickel (Ni), copper (Cu), lead (Pb), zinc (Zn), ruthenium (Ru), palladium (Pd), cadmium (Cd), iridium (Ir), rhodium (Rh), platinum (Pt), lithium (Li), osmium (Os), mercury (Hg), arsenic (As), antimony (Sb), chromium (Cr), aluminum (Al), or a metal of the lanthanide series especially europium (Eu), ytterbium (Yb), cerium (Ce), a metal catalyst whose metal(s) is/are selected from metals from said material and whose metal(s) present in the composition of the invention come(s) exclusively from the material of plant origin and without the addition of metal from a source other than said material for the implementation of organic synthesis reactions involving said catalyst.

Preferably, the reactions used in the method of the invention are chosen from among:
the coupling reactions, preferably chosen from among;
coupling reactions between heterocyclic or non-heterocyclic brominated derivatives with boronic acids such as the Suzuki reaction;
Heck's reaction;
Sonogashira's reaction;
polymer construction reactions such as polycondensations,
the reduction reactions, chosen, in particular, from among:
the enone reduction reaction;
the reduction reaction of a carbonyl derivative;
the isomerization reaction of an exocyclic double bond;
the oxidation reactions, preferably chosen from the oxidation of alcohols;
the oxidative halogenation reactions;
the electrophilic substitution reactions, such as nitration or thiocyanation reactions;
the condensation reactions, preferably condensation of a carbanion on a carbonyl compound (Doebner-Knoevenagel type reaction);
the multi-component reactions such as the Biginelli reaction; and
the oxidation reactions of alkenes such as epoxidation and oxidative cleavage.

The object of the invention is also the use as described above or the method as described above comprising the preparation as catalyst of a composition containing a metal catalyst originating, optionally after acid treatment, from the ashes obtained by heat treatment of a material of plant origin in the form of a powder insoluble in water in sufficient quantity to fix at least 90%, 95% or preferably 100% of the metal(s) present in the liquid medium to be treated rich in phenolic acids, having fixed at least one metal in ionic form chosen, in particular, from scandium (Sc), manganese (Mn), iron (Fe), cobalt (Co), nickel (Ni), copper (Cu), lead (Pb), zinc (Zn), ruthenium (Ru), palladium (Pd), cadmium (Cd), iridium (Ir), rhodium (Rh), platinum (Pt), lithium (Li), osmium (Os), mercury (Hg), arsenic (As), antimony (Sb), chromium (Cr), aluminum (Al) or a metal of the series of lanthanides including europium (Eu), ytterbium (Yb), cerium (Ce), characterized in that the organic synthesis reactions involving said catalyst are selected from among:
oxidation reactions
cross-coupling reduction reactions
homocoupling reactions such as carbon-carbon bond formation reactions such as the Suzuki reaction, the Heck reaction, the Sonogashira reaction, the polymerizations, the polycondensations
the reactions involving an acidic Lewis catalysis preferably chosen from electrophilic aromatic substitution reactions (EASr), pericyclic reactions, multicomponent reactions, cascade reactions, addition reactions, transfunctionalization reactions, esterifications, carboxylations, halogenations, nitrations, thiocyanations, aldol reactions or crotonization or related reactions, preferably Knoevenagel reactions, Perkin reactions, Claisen reactions, Tollens reactions or Thorpe-Ziegler reactions
multi-step reactions comprising an oxidation or reduction reaction followed by Lewis acid catalysis
isomerization reactions Advantageously, the organic synthesis reactions may be catalyzed functional conversion reactions chosen from oxidation reactions such as Wacker-Tsuji oxidation, alcohol oxidation, oxidative coupling of aromatic compounds, reduction such as the reduction of olefins and nitro and nitrile compounds or the hydrosilylation of olefins and alkynes, catalytic hydrogenation, cross-coupling and homo-coupling such as carbon-carbon bond formation reactions such as the Suzuki reaction, the Heck reaction, the Sonogashira reaction, nucleophilic addition reactions of an enamine on pi-allylic complexes, Buchwald-Hartwig type reactions, carbonylation reactions and ene-reactions, regioselective reactions between an alkene and an aromatic derivative, cyclopropanation of alkenes, cycloadditions, cascade carbocylation polyunsaturated compounds, allyl isomerization, cycloaddition, ene-reactions, cycloisomerizations, hydroboration, polymerization reactions, polycondensations, syntheses of unsaturated and conjugated polymers.

Even more preferably, the organic synthesis reactions are chosen from the following reactions: oxidation reactions, reduction reactions, cross-coupling and homocoupling reactions, reactions involving Lewis acid catalysis, preferably chosen from electrophilic aromatic substitution reactions (EASr), pericyclic reactions, multicomponent reactions, cascade reactions, addition reactions, halogenations, aldolization or crotonization reactions or related reactions such as condensation reactions of an aldehyde on a Knoevenagel type di-activated compound, the Perkin reaction, the Tollens reaction, the Thorpe reaction, the Claisen reaction, or the Mukaiyama reaction; oxidation or Lewis acid-catalyzed reduction reactions, brominations, protections such as chemoselective tritylations of alcohols and amines, acylations, in particular the acetylations of alcohols, phenols, thiols and amines, silylations of alcohols, oximes, enolates, phenols, amines and anilines, the formation of imines or amines, the deprotection of functions including detritylation, concerted rearrangements such as reactions or cycloadditions, pinacol or Beckmann transposition, Claisen-Schmidt reaction, Mukaiyama reaction or Knoevenagel-type reactions, dehydration or transfunctionalization reactions such as transamination or transtritylation reactions, reactions for the preparation of polyheterocyclic structures such as porphyrinogens or dithienylpyrroles, multicomponent reactions such as Triazole synthesis reactions, Hantzsch reactions, syntheses of optionally substituted piperidines, biomimetic reactions and hydride transfer reactions, even more preferentially among oxidation reactions, reduction reactions, coupling reactions. cross-coupling and homocoupling reactions, electrophilic aromatic substitution reactions (EASr), pericyclic reactions, multicomponent reactions, cascade reactions, addition reactions, halogenations, aldolisation or crotonization reactions or related reactions such as aldehyde condensation reactions on a Knoevenagel-type di-activated compound, the Perkin reaction, the Tollens reaction, the Thorpe reaction, the Claisen reaction, or the Mukaiyama reaction; oxidation or combination reduction reactions, electrophilic aromatic substitution reactions, the construction of heterocycles, the preparation and protection of carbonyl derivatives, radical oxidation, epoxidation, the oxidation of alcohols located in alpha of an aromatic group heterocyclic or carbocyclic or a double bond, the oxidative cleavages of polyols, the oxidation of benzamines, the aromatic oxidative dehydrogenation of unsaturated cyclic derivatives and/or conjugates optionally comprising a heteroatom, the direct halogenation of enolizable compounds, the reaction of Hantzsch in Lewis acid catalysis between an aldehyde, a beta-dicarbonyl compound and an ammonium source leading to the formation of dihydropyridines (DHP); advantageously among the reduction reactions, the cross-coupling and homocoupling reactions, the reactions involving a Lewis acid catalysis chosen preferably from electrophilic aromatic substitution reactions (EASr), pericyclic reactions, multicomponent reactions, reactions in cascade, addition reactions, halogenations, aldolization or crotonization reactions or related reactions such as the condensation reactions of an aldehyde on a di-activated Knoevenagel-type compound, the Perkin reaction, the Tollens reaction, Thorpe's reaction, Claisen's reaction, or Mukaiyama's reaction; halogenation reactions, in particular halogenation of primary, secondary and tertiary alcohols (Lucas reaction), electrophilic aromatic reactions in series, substitutions or additions, Friedel-Crafts alkylations, preferably the reaction between toluene and chloride of benzyl to obtain 4- and 2-methyldiphenylmethane, Friedel-Crafts acylations, preferably methylacetophenone synthesis, multicomponent reactions, in particular the Biginelli reaction leading to the synthesis of dihydropyrimidinones or dihydrothiopyrimidinones, preferably 3,4-dihydropyrimidin-2(1H)-one or 3,4-dihydropyrimidin-2(1H)-thione, and the Hantzsch reaction preferably used to prepare the dihydropyridines, the synthesis of 5-ethoxycarbonyl-6-methyl 4-isobutyl-3,4-dihydropyrimidin-2(1H)-one, the reaction between 3-hydroxybenzaldehyde, ethyl 3-ketopentanoate and thiourea to obtain the Ethyl 6-methyl-4-(3-hydroxyphenyl)-2-thioxo-1,2,3,4-tetrahydropyrimidine-5-carboxylate (monastrol), cycloaddition reactions, in particular the Diels-Alder reaction such as the reaction of cyclopentadiene with diethyl fumarate or the reaction of 3-buten-2-one with 2,3-dimethyl-1,3-butadiene, the transesterification reactions, preferably the reaction of methyl palmitate and butan-1-ol, the synthesis of amino acid complexes or oximes, preferably $Cu^{2+}$ complexes of oximes, catalyzed hydrolysis of organosulfurized functions, in particular thiophosphates such as parathion, synthetic reactions of catalyst for hydrogenation reactions after reduction of Ni(II) to Ni(0), reduction reactions such as reduction of 1-phenyl-2-nitroprene to 1-phenyl-2-aminopropane, coupling reactions comprising cross-coupling reactions, especially the Suzuki reaction to synthesize preferably diaryl compounds such as 3-methoxy-4'-methylbiphenyl, the Heck reaction, and the Ullmann reaction (especially aromatic nucleophilic substitutions such as N and O-arylations), the condensation of diamines on carbonyl derivatives, in particular the synthesis of 1-H-1,5-benzodiazepines preferably from o-phenylenediamine and acetone, the chemoselective hydrolysis of methyl esters in peptide chemistry, in particular deprotection of carbonyl groups without cleavage of Fmoc, Fmoc-Gly-OMe and Fmoc-Gly-Phe-Pro-OMe, the chemoselective hydrolysis of the methyl ester 6,7-dideoxy-1,2:3,4-di-O-isopropyldine-7-[(9-fluorenylmethoxycarbonyl)-amino]-D-glycero-α-D-galacto-octopyranuronic to obtain a galactose-derived amino acid, synthesis of 5'-protected oligonucleotides, synthesis of 5'-GpppT6 and 5'-GpppRNAs, the coupling of phosphoroimidazolidate T6 on a solid support with GDP in particular the synthesis of 5'-guanosyl triphosphate hexa-2'-deoxythymidylate (GpppT6), the reductive amination, preferably the catalysed formation of imines followed by their reduction in situ, the synthesis of secondary amines and substituted anilines, the chlorination of alkenes such as the chlorination of dicyclopentadiene, aromatic halogenation reactions without dihalogen, nitration reactions without nitric and sulfuric acid, thiocyanation reactions, synthesis of bromo- and iodoanisole, successive or cascade reactions such as addition, dehydration, cycloaddition, or electrocyclization reactions, the synthesis of debtenzopyrans and cannabinoids or dihydrocannabinoids and, in particular, the condensation of diamines on carbonyl derivatives, reductive aminations, aromatic halogenations without dihalogen, the Ullmann reaction, successive or cascade reactions such as addition, dehydration, cycloaddition or cyclization reactions, cross-coupling or non-cross-coupling reactions such as Suzuki reaction, electrophilic aromatic reactions in series, substitutions or additions, multicomponent reactions, in particular the Biginelli reaction.

The object of the invention is also a method for recycling metal catalysts, in particular metal catalysts comprising at least one metal in ionic form chosen, in particular, from scandium (Sc), manganese (Mn), iron (Fe), cobalt (Co), nickel (Ni), copper (Cu), lead (Pb), zinc (Zn), ruthenium (Ru), palladium (Pd), cadmium (Cd), iridium (Ir), rhodium (Rh), platinum (Pt), lithium (Li), osmium (Os), mercury (Hg), arsenic (As), antimony (Sb), chromium (Cr), aluminum (Al) or a metal of the lanthanide series, in particular europium (Eu), ytterbium (Yb), cerium (Ce), said method being characterized by the following steps:

- a treatment of a reaction medium in which a chemical reaction using said soluble metal catalyst has been carried out, with a material of plant origin rich in phenolic acids in the form of a powder insoluble in water in an amount sufficient to fix at least 90%, 95% or preferably 100% of the metal(s) in ionic form present in the reaction medium to be treated, and
- filtration for recovering said material of plant origin rich in phenolic acids having fixed the metal(s) in ionic form present in the reaction medium,
- heat treatment of said material of plant origin rich in phenolic acids, having fixed the metal(s) in ionic form to obtain ashes constituting the recycled metal catalyst comprising at least one metal in ionic form chosen, in particular, from scandium (Sc), manganese (Mn), iron (Fe), cobalt (Co), nickel (Ni), copper (Cu), lead (Pb), zinc (Zn), ruthenium (Ru), palladium (Pd), cadmium (Cd), iridium (Ir), rhodium (Rh), platinum (Pt), lithium (Li), osmium (Os), mercury (Hg), arsenic (As), antimony (Sb), chromium (Cr), aluminum (Al) or a metal of the lanthanide series including europium (Eu), ytterbium (Yb), cerium (Ce).

The recovery of plant-based materials having fixed at least one metal offers at least one advantage over previous implementations of materials of plant origin which have fixed metal cations to obtain biocatalysts:

The materials of plant origin which have fixed at least one metal of the present invention make it possible to carry out organic synthesis reactions in the presence of said materials in homogeneous recyclable phase, whereas, generally, homogeneous catalysis does not make it possible to separate the catalyst from the reaction medium, because the catalyst is in the same phase as the reactants and the products of the catalyzed reaction. Thanks to the materials of the invention, the metal catalyst is easily recoverable by bringing into contact a material of plant origin in the form of a plant waste powder, for example from the roots of certain aquatic plants (examples: roots of water hyacinths or water lettuce), vegetable waste rich in tannins (examples: coffee and tea grounds) or vegetable waste rich in lignin (wheat straw, pine cones, coconut husks) with the reaction medium after catalysis to recover the complex metal/material of plant origin rich in phenolic acids which may be isolated by simple filtration and rinsing, thus the bio-sourced catalysts in the homogeneous phase of the present invention are recyclable.

Moreover, the performance of materials of plant origin having fixed at least one metal of the invention are often higher than those of their commercial counterparts of non-plant origin. In fact, the materials of the present invention have a better catalytic activity. For example, the material according to the invention comprising at least palladium is active starting from 0.001 mol %, preferably from 0.0025 to 0.01 mol % palladium in M(II) form.

The present invention makes it possible to recover materials of plant origin while providing a chemical reaction catalyst material.

The present invention makes it possible to recover materials of plant origin while recycling metals.

The present invention makes it possible to recover materials of plant origin while removing pollutants containing one or more metals.

The invention will now be described by means of the following non-limiting examples.

Example 1: Recycling of Palladium (Pd)

Example 1.1

Study of the variation in Pd in different amounts of root extracts of water hyacinths, air dried, ground and screened on a sieve with 1.5 mm mesh openings in a solution comprising 14 mg/l in Pd at pH=2.5-3. The concentration of root extract (RE) was varied from 1 g/l to 2 g/l, and the duration of contacting from 30 min to 2 hours. The root extracts are heat treated at 550° C. before analysis. The results are shown in Table 2.

TABLE 2

| Recycling of palladium | | |
|---|---|---|
| Label | variable | Pd |
| Initial concentration in effluent | mg/l | 14.25 |
| Metal content in root extract after biosorption (RE) 1 g/l, 0.5 h | % weight | 20.38 |
| RE 1 g/l, 2 h | % weight | 23.76 |
| RE 1.5 g/l, 0.5 h | % weight | 15.19 |
| RE 1.5 g/l, 2 h | % weight | 17.74 |
| RE 2 g/l, 0.5 h | % weight | 11.99 |
| RE 2 g/l, 2 h | % weight | 13.88 |

Example 1.2

Study of the quantity of Pd remaining in the effluent after coming into contact with different amounts of root extracts of water hyacinths placed in a 14 mg/l solution in Pd, at a pH of 2.5-3 and with a biomass/effluent volume ratio of 0.2 g/0.21.

TABLE 3

| Pd concentration in an effluent brought into contact with a root extract of water hyacinth. | | |
|---|---|---|
| Label | variable | Pd |
| Treated solution 1 g/l, 0.5 h | mg/l | 2.09 |
| Treated solution 1 g/l, 2 h | mg/l | 1.59 |
| Treated solution 1.5 g/l, 0.5 h | mg/l | 1.51 |
| Treated solution 1.5 g/l, 2 h | mg/l | 0.01 |
| Treated solution 2 g/l, 0.5 h | mg/l | 0.04 |
| Treated solution 2 g/l, 2 h | mg/l | 0 |

Materials from water hyacinth roots can achieve total decontamination of effluents.

Example 1.3 (Comparative)

Rhizofiltration using live water hyacinth (1.5 g) roots on a solution of 200 ml at 14 mg/l of Pd and study of the variation in elements over time in the root extracts and in the solution

TABLE 4

| Rhizofiltration | | |
|---|---|---|
| Label | variable | Pd |
| Initial solution at t = 0 | mg/l | 14.18 |
| Treated solution at t = 0.5 h | mg/l | 8.49 |

TABLE 4-continued

| Rhizofiltration | | |
|---|---|---|
| Label | variable | Pd |
| Treated solution at t = 2 h | mg/l | 4.74 |
| Roots at t = 0.5 h | % weight | 7.64 |
| Roots at t = 2 h | % weight | 21.44 |

Example 1.4: Comparison of Pd Biosorption Between Various Parts of Water Hyacinths and Various Operating Conditions The method is optimized by using dehydrated water hyacinth roots and using root tips (without stems) as the results in the table below show (element levels are in mg/l for initial effluent and in % by weight for the rest of the results, the ratio biomass/volume of effluent is at least 1 g/1):

TABLE 5

Comparison of biosorption Pd between different parts of water hyacinths and different operating conditions, palladium content.

| Label | variable | Pd |
|---|---|---|
| Initial effluent | mg/l | 14 |
| Effluent after biosorption - whole hyacinth (5 g/l) | mg/l | 5.19 |
| Residual whole hyacinth extract after biosorption (5 g/l) | % weight | 1.47 |
| Effluent after biosorption - drained fresh roots (5 g/l) | mg/l | 3.90 |
| Root extract of fresh roots drained after biosorption (5 g/l) | % weight | 2.39 |
| Effluent after biosorption - ungrounf and dehydrated roots (1 g/l) | mg/l | 7.70 |
| Unground and dehydrated root extract after biosorption (1 g/l) | % weight | 13.90 |
| Effluent after biosorption - fresh ungrounf roots (1 g/l) | mg/l | 6.70 |
| Root extract derived from ungrounf fresh roots after biosorption (1 g/l) | % weight | 6.60 |
| Effluent after biosorption - ungrounf and air-dried roots (1 g/l) | mg/l | 3.93 |
| Root extract from ungrounf and air-dried roots after biosorption (1 g/l) | % weight | 12.62 |
| Effluent after biosorption - stems (without small roots) (1 g/l) | mg/l | 8.33 |
| Extract derived from the stems after biosorption (1 g/L) | % weight | 3.64 |
| Extract derived from small roots (without stem) after biosorption (1 g/l) | % weight | 21.87 |
| Effluent after biosorption - small roots (without stem) (1 g/l) | mg/l | 0.91 |
| Effluent after biosorption using hyacinth root powder (1 g/l) | mg/l | 5.39 |

Example 1.5: Comparison of Biosorption of Pd from Other Materials

Other materials of plant orgin rich in phenolic acids (wheat straw) and lignin have been tested for comparative purposes. These materials have not been functionalized. The results obtained are shown in the table below (the element levels are in mg/l for the initial effluent and in % by weight for the rest of the results):

TABLE 6

Comparison of biosorption of Pd from other materials of plant origin

| Label | variable | Pd |
|---|---|---|
| Initial effluent mg/L | mg/l | 14.51 |
| Effluent after biosorption (wheat straw powder 5 g/l) | mg/l | 3.38 |
| Wheat straw extract after biosorption | % weight | 2.96 |
| Effluent after biosorption (lignin derived from wheat straw 1 g/l) | mg/l | 1.63 |
| Lignin extract after biosorption | % weight | 6.67 |
| Effluent after extraction - heat treated lignin 1 g/l | mg/l | 1.61 |
| Lignin extract - heat treated after biosorption 1 g/L | % weight | 3.26 |
| Effluent after biosorption (pine cone powder) 1 g/l | mg/l | 1.09 |
| Effluent after biosorption (water lettuce root powder 1 g/l | mg/l | 0.96 |
| Effluent after biosorption (cellulose 1 g/l) | mg/l | 11.8 |
| Effluent after biosorption (green algae powder 1 g/l) | mg/l | 9.1 |

The percentages of fixed Pd are lower than those of dehydrated hyacinth root powder. However, the heat treatment used does not completely destroy lignin, unlike cellulose. The "catalytic activity" part is the decisive parameter making it possible to appreciate the interest of these materials of plant origin.

The use of a material of plant origin of different composition (tannin instead of phenolic polymers) is a complementary solution. It leads to catalysts of more conventional composition i.e. monometallic. This possibility is illustrated with the coffee grounds.

TABLE 7

Brining coffee grounds into contact with an effluent

| Label | Weight of coffees grounds (g/l) | variable | Pd content |
|---|---|---|---|
| Initial effluent | — | mg/l | 14.46 |
| Effluent after biosorption | 1 g/l | mg/l | 12.03 |
| Ash after biosorption | — | % weight | 50.81 |
| Effluent after biosorption | 5 g/l | mg/l | 5.03 |
| Ash after biosorption | — | % weight | 36.50 |
| Effluent after biosorption | 5 g/l | mg/l | 1.05 |
| Coffee grounds washed 3 times with water Effluent after biosorption | 5 g/l | mg/l | 0.72 |
| Ash after biosorption | — | % weight | 59.48 |

The coffee grounds have remarkable chelating properties of Pd. It is possible to achieve very high rates of biosorption with 5 g/l of coffee grounds. Its heat treatment leads to a metal catalyst where the Pd is the most important element. Its metallic composition is different from that derived from the roots of aquatic and terrestrial plants. In the case of tannins such as coffee grounds, heat treatment leads to almost total destruction of organic matter.

The results obtained with powders derived from pine cones and water lettuce roots are spectacular: all Pd is extracted with 1 g of biomaterial, without prior functionalization (entries 8 and 9 of Table 6).

Example 2.1: Recycling of Manganese (Mn) and Iron (Fe)

Fe and Mn are the metallic elements of the chemistry of the future. The first is very abundant, inexpensive and nontoxic. Its catalytic properties are broad: oxidations, Lewis acids and coupling agents. Mn(II, III, IV) is an oxidizing agent that can advantageously replace the reagents and catalysts not meeting the REACH regulation. Their recycling is rarely mentioned. However, the discharge of loaded effluents into these metallic species is an environmental problem. In addition, according to the French PIPAME, the known and exploitable resources of Mn could be exhausted in about 40 years. Recycling is therefore useful and necessary. It also opens new opportunities in synthesis as evidenced by the examples presented.

The purification of an industrial effluent is always much more complex and difficult than that of a synthetic laboratory solution.

A study on the biosorption conditions shows that it is possible to extract the two elements Fe and Mn by adjusting the amount of material of plant origin. With 20 g/l of material of plant origin (hyacinth root powder), aluminum, zinc and nickel are totally adsorbed as well.

TABLE 7

Al, Ca, Mg, Mn, Fe, Zn and Ni contents in an effluent before and after contact with a root extract of water hyacinth.

| | variable | Al | Ca | Mg | Mn | Fe | Zn | Ni |
|---|---|---|---|---|---|---|---|---|
| Initial effluent | mg/l | 44.5 | 214 | 175 | 13.3 | 11.1 | 3.4 | 2.1 |
| Effluent after biosorption | mg/l | 0 | 209.1 | 134.5 | 0.8 | 0.3 | 0 | 0 |

An advantageous method for reducing the amount of biomass is made possible by neutralizing the industrial effluent.

Purification Procedure in Neutral Industrial Effluent Column:

One liter of industrial effluent (characterized by a pH between 2.5 and 3.5) was neutralized with sodium hydroxide (2M NaOH) to neutral pH, and then was passed through a column containing a non-functionalized water hyacinth powder. After 1 pass at room temperature (30 minutes), the powder is dried at 85° C. The dry residue is calcined at 550° C. to obtain a powder enriched in metals.

Flow has very little influence on the results. 20 l/h, 5 l/h and 2.5 l/h lead to similar results. Similarly, very low residence time is sufficient: 1 minute for 50 mL of effluent/ 12 g of biosorbent.

TABLE 8

Purification of one liter of neutral industrial effluent with 12 g of non-functionalized hyacinth powder

| Metal | Initial conc. in the effluent (mg/l) | Conc. in the effluent after passage 11, (mg/l) |
|---|---|---|
| Al | 4.2 | 0 |
| Ca | 51.9 | 81 |
| Fe | 7.2 | 0 |
| Mg | 50.5 | 38.6 |
| Mn | 11.4 | 0.2 |
| Zn | 2.3 | 0 |

The results show that Al, Fe, Mn and Zn are very strongly, if not totally, retained by the material of plant origin. The Mn level is compatible with the discharge standards (0.5 mg/l), the sum Fe+Al, Zn also (limits allowed: Fe+Al=5 mg/l, Zn=2 mg/l).

The following table shows the amount of biomass (water hyacinth powder) needed to biosorb 100% Mn depending on the initial concentration of Mn in the industrial effluent.

TABLE 9 amount of biomass needed to biosorb 100% Mn

| Mn content in the effluent | mg/L | 3 | 6 | 9 | 12 | 15 | 18 | 21 | 24 |
|---|---|---|---|---|---|---|---|---|---|
| Requires quantity of biomass | g | 2.3 | 5 | 8.6 | 13 | 18.5 | 24 | 28 | 30 |

In conclusion, the hyacinth root powder used under the conditions described makes it possible to simultaneously adsorb Fe, Al, Zn and Mn and to meet the standards of discharge in the environment. (Mn=0.5 mg/l).

The discharge of effluents loaded with Mn and Fe is an environmental problem.

Example 2.2. Iron Recycling

Industrial media with high levels of Fe and Mn were treated with root extracts of dehydrated and ground water hyacinths. These roots are then heat treated at 500° C. Once the mineralization has been carried out, the analyses are carried out in Inductively-Coupled Plasma Mass Spectrometry (ICP-MS). With 1 g/L of biomass, it is possible to extract more than 95% of iron. The results are summarized in the table below and illustrate the possibility of a selective extraction of Fe in the presence of Mn.

TABLE 10

Selective extraction of Fe in the presence of Mn

| Label | variable | Na | Mg | Al | K | Ca | Mn | Fe |
|---|---|---|---|---|---|---|---|---|
| Initial effluent | mg/l | 13 | 123 | 41 | 2.8 | 155 | 9 | 6.2 |
| Effluent after biosorption | mg/ll | 16 | 107 | 34 | 8 | 148 | 7 | 0.3 |
| Root extract | ppm | 68848 | 37871 | 25342 | 98207 | 25342 | 2288 | 55790 |
| Root extract | % weight | 6.88 | 3.79 | 2.53 | 9.82 | 2.53 | 0.23 | 5.58 |

With regard to calcined root extracts, the accumulation of Mn is low (0.23%). With regard to iron, the quantity is more significant (5.58%), the proportions in the ashes are consistent with the very low concentration of metals remaining in the effluent (0.6%). Biosorption is thus very effective. The amount of aluminum in the ashes is not negligible (3.2% for the concentrated effluent and 2.5% for the untreated effluent) because this element has very interesting properties when it is in the form of aluminum chloride ($AlCl_3$). It is a potent Lewis acid that has many applications in the chemical industry as a catalyst for electrophilic aromatic substitution reactions.

A study on the biosorption conditions shows that it is possible to extract the two elements Fe and Mn by increasing the duration of the biosorption or the amount of biomass. With 20 g/l of biomass (hyacinth root powder), aluminum, zinc and nickel are totally adsorbed as well.

TABLE 11

Concentration of metals in the effluent

| | variable | Al | Ca | Mg | Mn | Fe | Zn | Ni |
|---|---|---|---|---|---|---|---|---|
| Initial effluent | mg/l | 44.5 | 214 | 175 | 13.25 | 11.14 | 3.4 | 2.1 |
| Effluent after biosorption | mg/l | 0 | 209.1 | 134.47 | 0.82 | 0.29 | 0 | 0 |

In conclusion, the hyacinth root powder used under the conditions described makes it possible to simultaneously adsorb Fe, Al, Zn and Ni and Mn. It is also possible to sequentially biosorb Fe, Al, Zn, Ni, then Mn. This example shows that the Fe may be extracted before and without the Mn if the amount of material of plant origin is low.

Example 3: Ni Recycling

The biosorption was carried out on an effluent comprising nickel in the form of $NiSO_4$ (15 mg/l of Ni). Absorption is performed with pine cone powder and water lettuce root powder.

Preparation of the pine cone powder: A pine cone is roughly cut, then washed in 100 mL of iPrOH. After 30 minutes, the pine cone is filtered, dried at room temperature, ground and sieved through the sieve with 1.5 mm mesh openings. The powder obtained is used in the biosorption.

Preparation of the water lettuce powder: The lettuce roots are air-dried at room temperature until they become a stable mass, then they are ground and sieved with a sieve with 1.5 mm mesh openings. The powder obtained is used directly in the extraction of metals.

Procedure: 1 g of material of plant origin is added to 1 liter of a solution consisting of $NiSO_4$ (15 mg/l of Ni). The mixture is stirred for 2 h and then filtered. The solid is dried at 85° C. overnight. The dry solid obtained is then heat treated at 550° C. for 6 hours in order to obtain the ash enriched with metals.

TABLE 12

Extraction of nickel with pine cone powder (A) and water lettuce root powder (B)

| Initial Ni conc in the effluent, mg/l | Ni conc in the effluent, contacting with A (mg/l) | Ni conc. in the effluent after contact with B (mg/l) |
|---|---|---|
| 15 | <1 | <1 |

Example 4.1: Decontamination of Water Contaminated with Arsenic

An innovative solution for the decontamination of water polluted with arsenic is proposed. It is based on a bio-inspired solution. The principle consists in reconstituting the natural affinity of arsenic for the Mn and Fe oxides from the biomass saturated with these elements during the decontamination of an effluent having decontaminated a pyrite quarry effluent. The biomasses are heat treated (550° C. for 6 h) before use.

Procedure for the decontamination of pyrite quarry effluents: A material of plant origin, for example water hyacinth powder or pine cone powder modified by esterification autocatalysed with succinic acid, is disposed in a column. An industrial effluent containing Mn (effluents from the pyrite quarries) is introduced into this column. The effluent that has been brought into contact with the material of plant origin is recovered in an Erlenmeyer flask. This effluent meets the discharge standards for Mn and Fe/Al. The material of plant origin comprising mixed oxides (Fe, Mn, Al) is recovered, dried at 85° C., and heat-treated at 550° C. before being used as a plant filter.

Procedure for decontaminating a water comprising arsenic: A plant filter resulting from the decontamination of the effluent from a pyrite quarry and having been heat treated (550° C. 6 h), is arranged in a column and then is washed with distilled water. A solution comprising arsenic is introduced into this column filled with the plant filter. The water which has been brought into contact with the plant filter is recovered in an Erlenmeyer flask. The solution at the column outlet is collected and analyzed via ICP-MS and meets the discharge standards for As.

The amount of biomass required to obtain 1 g of metal-enriched solid residues:
A) Case A: 9.4 g of biomass
B) Case B: 6.7 g of biomass

TABLE 13

Composition of heat treated hyacinth root powders used to purify two different quarry effluents of pyrites A and B

| % weight | Al | Ca | Fe | Mn | Zn |
|---|---|---|---|---|---|
| Case A | 0.4 | 21 | 1 | 0.8 | 0.2 |
| Case B | 4 | 29 | 0.9 | 0.8 | 0.3 |

The two compositions differ essentially by the percentage of Al or even Ca. The Mn er Fe levels are very close. It should be remembered that the 3 treatments described in the literature and used in the natural environment are: $Al_2O_3$, $Fe(O)OH$, $MnO_2$.

TABLE 14 summary of the purification of the synthetic effluent with 5 g/l of heat treated powders from the biomass used to treat the effluents

| Origin of the biosorbant | Initial concentration of As, mg/l | Final concentration of As, mg/l | Flow, ml/min |
|---|---|---|---|
| Case A | 1.5 | <0.001 | 100/20 |
| Case B | 1.5 | 0.04 | 100/20 |
| Case B | 14 | 0.006 | 100/60 |
| Case B | 14 | 0.08 | 100/90 |

In this case, the adsorption of As is very sensitive to the flow rate. The slower the flow, the better the biosorption. Cases A and B meet environmental discharge standards (0.05 mg/l); case A also meets WHO drinking water standards (0.01 mg/l).

It is therefore possible to directly recover a plant filter filled with Mn/Fe in a purifying filter of water contaminated with As. These results are unexpected, because the heat treatment used to generate the ash being at 550° C., the manganese present may be in the form of $Mn^{III}$, according to Manganese Compounds, Ullmann Encyclopedia of Industrial Chemistry 7th Ed. This is not the known form for adsorbing As, $MnO_2$. Fe levels are identical and do not explain these results. Higher % Al decreases the adsorption performance of As, suggesting that aluminum is not in the form of alumina, known for its As adsorption activity.

Given the polymetallic composition of the material of plant origin, mixed oxides can explain such a result. XRD and X-absorption studies have demonstrated the presence of a mixed oxide of calcium and manganese in heat treated Phyto-Mn: $Ca_2Mn_3O_8$. These results show that the passage through a material of plant origin does not lead to a simple juxtaposition of metal elements, but to a complex mixture that is different from conventional systems.

Example 4.2. Decontamination of a Solution Including Phosphates

The same method as that of Example 4.1 is adaptable to phosphate: plant filter resulting from the purification of the effluent from a pyrite quarry and comprising Mn and Fe and heat treated at 550° C. allows concentration of 21 mg/l of disodium monohydrogenphosphate from a solution loaded at 25 mg/l.

Example 5: Recycling Zn

Zinc is an essential mineral in many applications. The world's exploitable Zn resources could be exhausted in 17 years (Pitron, The Rare Metal War, LLI, 2018). Developing recycling methods is a topical issue. It is proposed to show how structural materials rich in phenolic acids can solve this key problem. The demonstration is made using industrial effluents corresponding to real, complex, polymetallic cases, and not simple and reconstituted synthetic solutions.

Procedure for Purification of a Batch of Mining Effluent:

The material of plant origin is added to 1 liter of a solution generated by the infiltration of water in mining galleries having exploited a zinc ore. The mixture is stirred for 2 h and then filtered. The solid is dried at 85° C. overnight. The dry solid obtained is then heat treated at 550° C. for 6 hours in order to obtain the ash enriched with metals.

Procedure for Purifying the Same Mining Effluent in a Column:

The material of plant origin is put in a column, washed with water to moisten it. Then, 1 liter of effluent is eluted in a column with a flow rate of 3 l/h. The mixture is stirred for 2 h and then filtered. The purified solution is analyzed by MP-AES. The biomass is dried at 85° C. overnight, and then heat treated at 550° C. for 6 hours to obtain the metal enriched ash.

TABLE 15

Summary of the purification of the mining effluent rich in Zn (12.5 mg/l) and in Fe (5 mg/l):

| Biomasse | Weight, g/l | Final Zn concentration Zn in the effluent, mg/l |
|---|---|---|
| — | — | 12.5 |
| HRP* | 3 | 1 |
| HRP* | 5 | 0.6 |
| HRP in column | 3 | 1 |
| PCP*** | 5 | 3 |
| Resin acids*** | 5 | 3 |

*HRP—hyacnth roots powder
** PCP—pine cone powder
***Resin acids extracted from isopropanol from pine cones The mining effluent containing Zn at 12 mg/l can be purified with 3 g of water hyacinth root powder. Purified water contains around 1 ppm Zn which is below the permitted discharge standards (2 mg/l). Pine cones and resin acids alone are very close to the acceptable limit value. Their interest is to immediately retain iron, which is no longer detected after filtration. Ground pine cones can therefore serve as a pre-filter plant.

Example 6: Functionalization of Materials of Plant Origin and Biosorption

The affinity of the transition metals for phenolic biomaterials varies depending on the chemical structure of the cation to be complexed. Thus, for example, the affinity of palladium (Pd) for hyacinth powder, water lettuce and pine cone is exceptional. The situation is very different with ruthenium (Ru), iridum or nickel (Ni). Thus, other tests were carried out after functionalization of biomaterials, in order to increase the affinity of this type of cation for the material of plant origin (biosorbent). This approach is innovative because it leads to recovering common plant raw materials in an original way. The example of lignin is striking: a lot of research is devoted to the depolymerization of lignin and the production of small aromatic molecules. The objective is based on a new type of lignin recovery: its use as an eco-support material to recycle organic synthesis catalysts and clean up effluents.

The functionalization of natural phenolic acids is based on the principles of phenol chemistry and acid-derived functions adapted to that of polymers.

A possible functionalization mode is described: it is based on a carboxylation reaction of the hydroxyl functional groups making it possible to introduce a functionalized ester bond or not. Examples of the literature describe the enrichment of materials of plant origin by the use of citric acid. The method described consists of impregnating the material in water, heating to 60° C. and then to 100° C. until the medium is concentrated, and then heating to 120° C. to cause the esterification of the hydroxyl functions of the material via the intermediate formation of citric anhydride (B. Zhu et al., J. Hazard, Mater 153 (2008) 300-308). The method suffers from several limitations: the removal of water is difficult and unfavorable to the formation of an anhydride; the decomposition of citric acid takes place at a higher temperature (150-170° C.: Journal of Thermal Analysis and calorimetry, 2011, Volume 104, Issue 2, pp. 731-73) and the formation of citric anhydride is a minor product of the thermal decomposition of citric acid (Biomacromolecules 2007, 8, 3860-3870). The methods described here overcome these limitations by replacing the water with green solvents which are easier to remove (alcohols, ideally ethyl acetate), using a carboxylic anhydride and allowing a high degree of functionalization of the dicarboxylic acid materials of plant origin. The reaction is controlled, in order to limit the formation of fractions soluble in water and of no interest, to decontaminate the water. The acid anhydrides may be functionalized or not. They may be cyclic or aliphatic. They make it possible to introduce carboxylic acid, sulphonic acid, phosphonic acid, carboxylic ester or amide functional groups under more efficient conditions. Direct esterification reactions by autocatalysis (without passing through an intermediate anhydride) are also possible, but again water is to be avoided. Different natural polyacids are possible The direct esterification reactions were carried out by autocatalysis using polyacids, functionalized or not, and preferably in a non-aqueous medium. The most effective reagent-catalysts have the following general formula:

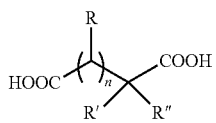

n=0, 1, 2; R=H, OH, $NH_2$, alkyl, aryl, $CH_2SR'''$, R'=H, COOH, COOR, $CH_2COOH$, NH-alkyl, NH-aryl, $NAr_2$, $NH_2$, OH, R''=H, OH, NH-alkyl, NH-aryl, $NAr_2$, $NH_2$.

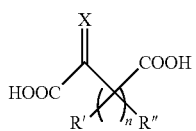

n=0, 1, 2; X=O, NR (R=H, OH, alkyl, aryl), R'=H, COOH, COOR, $CH_2COOH$, NH-alkyl, NH-aryl, $NAr_2$, $NH_2$, OH, R''=H, OH, NH-alkyl, NH-aryl, $NAr_2$, $NH_2$.

Functionalization of the plant material is also performed by acid anhydrides previously prepared or generated in situ at a temperature greater than or equal to 150° C.

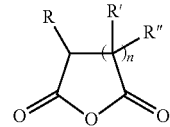

n=1, 2; R=H, OH, $NH_3^+$, $NR_3^+$, alkyl, aryl, $P(O)OR'_2$, $S(O)OR'_2$, R'=H, OH, $NH_3^+$, $NR_3^+$, alkyl, aryl, $P(O)OR'_2$, $S(O)OR'_2$.

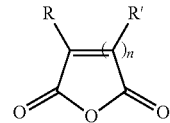

n=1, 2; R=H, OH, $NH_3^+$, $NR_3^+$, alkyl, aryl, $P(O)OR'_2$, $S(O)OR'_2$, R'=H, OH, $NH_3^+$, $NR_3^+$, alkyl, aryl, $P(O)OR'_2$, $S(O)OR'_2$.

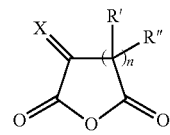

n=1, 2; X=O, NR'''(R'''=H, OH, alkyl, aryl), R'=H, R''=H, OH.

Examples 6.1: Carboxylation Via a Previously Prepared Anhydride: Example of Succinic Acid 3.2 g of succinic anhydride are solubilized in 34 ml of ethyl acetate. The mixture is refluxed until complete solubilization of anhydride, then 5 g of biomass are added to the solution. The suspension is stirred at reflux for 1 hour. The solvent is evaporated under reduced pressure and the solid is left at 120° C. for 1 night. After cooling to room temperature, 50 ml of distilled water is added to the solid and stirred for 15 minutes. The mixture is filtered and washed several times with distilled water (200 ml of distilled water for each wash under stirring 15 min before filtration) to neutral pH. The solid is recovered and dried at 85° C. for 1 night. Then, the functionalized material is suspended in 100 ml of distilled water and 2M NaOH is added to neutral pH. The solution is filtered and washed several times with distilled water until the colorless filtrate is obtained. The solid is dried at about 85° C.

Examples 6.2: Carboxylation by Direct Esterification and Autocatalysis: Example of Citric Acid 5 g of biomass are added to a flask with 4 g of citric acid in 20 ml of anhydrous ethanol. The mixture is stirred for 1 hour under reflux. The solvent is evaporated under reduced pressure and the solid is placed in the oven at 120° C. for 1 night. After cooling to room temperature, 50 ml of distilled water is added to the solid and stirred for 15 minutes. The mixture is filtered and washed several times with distilled water (200 ml of distilled water for each wash under stirring 15 min before filtration) to neutral pH. The solid is recovered and put in the oven at 85° C. for 1 night. Then, the functionalized biomass is suspended in 100 ml of distilled water and the 2M NaOH is added to neutral pH. The solution is filtered and washed several times with distilled water until the colorless filtrate is obtained. The solid is put in the oven at 85° C.

Examples 6.3: Carboxylation by Direct Esterification and Autocatalysis: Example of Glutaric Acid 5 g of biomass are added to a flask with 3.2 g of glutaric acid in 20 ml of ethyl acetate. The mixture is stirred for 1 hour under reflux. The solvent is evaporated under reduced pressure and the solid is placed in the oven at 120° C. for 8 h. After cooling to room temperature, 50 ml of distilled water is added to the solid and stirred for 15 minutes. The mixture is filtered and washed several times with distilled water (200 ml of distilled water for each wash under stirring 15 min before filtration) to neutral pH. The solid is recovered and put in the oven at 85° C. for 1 night. Then, the functionalized biomass is suspended in 100 ml of distilled water and the 2M NaOH is added to neutral pH. The solution is filtered and washed several times with distilled water until the colorless filtrate is obtained. The solid is put in the oven at 85° C.

Various examples of carboxylation are described in the following paragraph. A basic treatment makes it possible to generate the carboxylates and to reinforce the complexing nature of the biosorbent. Diacids such as succinic and glutaric derivatives are interesting because the carbon number limits the solubilization of carboxylates in water. The yield is greatly improved.

Examples 6.4: Carboxylation Using Lemon Juice 1 g of washed coffee grounds is added to 25 ml of juice of a freshly squeezed lemon. The reaction mixture is gradually heated to 100° C. and maintained until the dry solid is obtained. The product is dried at 120° C. overnight. Then, the solid is washed several times (up to pH=6-7) with distilled water. After thoroughly washing the biosorbent with water, 2M NaOH is added until pH=7, the solid is filtered and washed several times (to neutral pH) with water. The functionalized biosorbent is dried at 85° C. for 12 hours, then analyzed in IR. The degree of grafting is important, but lower than that obtained by isolated citric acid.

In order to determine the degree of functionalization of the functionalized materials, a titration of the carboxylic acid functions with a 2M NaOH aqueous solution was carried out. All data are grouped in Table 16.

The measurement of band intensities is performed to assess the need or not to functionalize the biomass. A control after functionalization leads to the following data:

TABLE 16

IR analysis of plant materials before and after functionalization

| Functionalized materials | IR data of the C=O band of the COOH group (cm$^{-1}$) | IR data of the aromatic cycle (cm$^{-1}$) | Absorbance difference ratio ($\Delta T$) between functional groups C=O/Ar |
| --- | --- | --- | --- |
| Hyacinth root powder functionalized with succinic anhydride/ AcOEt | 1680 ($\Delta T$ = 12.3%) | 1513 ($\Delta T$ = 7.2%)<br>1410 ($\Delta T$ = 11.1%) | 1.7<br>1.1 |
| Coffee grounds functionalized with succinic anhydride/ AcOEt | 1660 ($\Delta T$ = 2.5%) | 1517 ($\Delta T$ = 1.7%) | 1.5 |
| Pine cone powder functionalized with succinic anhydride/ AcOEt | 1641 ($\Delta T$ = 2.7%) | 1512 ($\Delta T$ = 2.1%) | 1.3 |
| Pine bark powder functionalized with succinic anhydride/ AcOEt | 1607 ($\Delta T$ = 12%) | 1512 ($\Delta T$ = 7.7%) | 1.6 |
| Pine cone powder functionalized with citric acid/EtOH | 1613 ($\Delta T$ = 0.95%) | 1511 ($\Delta T$ = 0.42%) | 2.3 |
| Coffee grounds functionalized with citric acid/EtOH | 1660 ($\Delta T$ = 14%) | 1515 ($\Delta T$ = 10%)<br>1412 ($\Delta T$ = 13) | 1.5<br>1.1 |

It should be noted that the functionalization also results in the formation of a C=O band attributed to the carboxylic ester group formed Example 6.5: Esterification with a Simple Alcohol The esterification of the COOH groups of the biosorbant of plant origin may be carried out with a simple aliphatic alcohol such as methanol or ethanol. Hyacinth root powder (5 g) is suspended in methanol (250 ml), acidified with an acid such as conc. $H_2SO_4$ acid (1 ml). The reaction mixture is refluxed for 12 h and then filtered at room temperature. The solid is washed several times with water (to neutral pH). The functionalized biosorbent is dried at 85° C. for 12 hours.

Example 6.6: Saponification

Many phenolic-rich biosorbents possess carboxylic ester functions. In order to increase the number of carboxylic acid functions, controlled hydrolysis of the ester functions is possible.

Procedure 10 g of pine cone powder are dissolved in 60 ml of 0.1M aqueous sodium hydroxide solution. The suspension is stirred for 4 h at 80° C. then cooled to room temperature, filtered, washed with water until neutral, and dried at 85° C.

Example 6.7. Transfonctionnalisation

Some phenolic biomaterials are naturally rich in carboxylic esters. This is, for example, green tea. This property can be exploited to transesterify or transfunctionalize the ester groups with polyfunctional ester or amide groups in order to enhance the affinity of the platinoids for the biosorbents. Amines, alcohols, aminosulfonates, aminophosphonates and amino alcohols were studied.

Example 6.7.1

Green tea powder previously washed with hot water (1 g) is suspended in ethanolamine at 110° C. (10 ml). The reaction mixture is refluxed for 6 h and then filtered at room temperature. The solid is washed several times with water. The functionalized biosorbent is dried at 85° C. for 12 hours.

Example 6.7.2

Green tea powder (1 g), previously washed with hot water, is suspended in tert-butanol and taurine (1 g) at 110° C. (35 ml). The reaction mixture is refluxed for 6 h and then filtered at room temperature. The solid is washed several times with water. The functionalized biosorbent is dried at 85° C. for 12 hours.

Example 6.7.3

Green tea powder (400 mg) previously washed with hot water is suspended in 2-dipicolylamine (4 ml) at 110° C. (35 ml). The reaction mixture is refluxed for 6 h and then filtered at room temperature. The solid is washed several times with water. The functionalized biosorbent is dried at 85° C. for 12 hours.

Example 8. Recycling of Pd with Functionalized Biomass

The functionalizations described previously are implemented to optimize the recycling of Pd. The different possibilities described above are directly compared.

Procedure for Batch Biosorption:

In an aqueous solution containing 14 ppm of Pd(II), 1 g of biomass is added and the mixture is stirred for 2 hours. The biomass is filtered, dried at 85° C. for 12 h and calcined at 550° C.

A) Hyacinth powder functionalized by esterification autocatalysed with citric acid.
B) Hyacinth powder functionalized by esterification autocatalysed with succinic acid.

The following table shows the concentration of palladium in the aqueous solution after contact with material A or B.

TABLE 17

Pd concentration in the effluent after contact with material A or B.

| | Pd conc., mg/l |
|---|---|
| Initial conc. in the effluent | 14 |
| Conc. in the effluent after contact with A | 0 |
| Conc. in the effluent after contact with B | 0 |

The modification of biomass increases the biosorption capacity of palladium. We are able to extract all the palladium from the solution after functionalization. The carboxylation and the esterification lead in each case to a total recycling of the Pd.

This approach may be extended to other biomaterials:

A) Ester functionalized coffee grounds autocatalysed with citric acid
B) Ester functionalized coffee grounds autocatalysed with succinic acid The following table shows the concentration in the aqueous solution after contact with biosorbent A or B.

TABLE 18

Pd concentration in the effluent after contact with material A or B.

| | Pd, mg/L |
|---|---|
| Initial conc. in the effluent | 14 |
| Conc. in the effluent after contact with A | 0 |
| Conc. in the effluent after contact with B | 0 |

The modification of the coffee grounds by the reaction improves the recycling of Pd (II). It is more than doubled in each case. The functionalizations by carboxylation (A, B) are very effective. In the 2 cases described, the extraction of Pd is total.

The best results with the functionalized biomass have been studied with higher palladium concentrations to test the limits of the method:

A) Biosorption of Pd in different concentrations with 1 g of hyacinth powder functionalized by esterification autocatalysed with citric acid/EtOH.

TABLE 19

Bisorption of Pd with hyacinth powder functionalized by esterification autocatalysed with citric acid/EtOH

| Initial conc. | After biosorption |
|---|---|
| 14 mg/l | 0 |
| 30 mg/l | 0 |
| 44 mg/l | 1 mg/l |

B) Biosorption of Pd in different concentrations with 1 g of hyacinth powder esterified with methyl alcohol.

TABLE 20

Bisorption of Pd with hyacinth powder esterified with methyl alcohol

| Initial conc. | After biosorption |
|---|---|
| 14 mg/l | 0 |
| 30 mg/l | 5 mg/l |

The extraction of palladium with the esterified biomass remains effective. We can accumulate 25 ppm of palladium under these conditions.

In order to be able to transpose the results on an industrial scale, we carried out the extraction in column (and no longer in batch) on a solution of 40 mg/l of Pd with 1 g of biomass (hyacinth powder acid esterified citric) for 1 liter of effluent.

Procedure for Column Biosorption:

1 g of biomass (hyacinth powder, which is functionalized with citric acid, is put in the column) The synthetic effluent (1 l) containing 40 mg of Pd is passed three times in the column The passage time of 1 l of solution is 35 min.

TABLE 21

Biosorption of Pd with hyacinth powder
functionalized with citric acid

|  | Pd, mg/l |
|---|---|
| Initial conc, | 41 |
| Pass 1 | 0 |
| Pass 2 | 0 |
| Pass 3 | 0 |

The complexation of palladium is remarkable. 41 ppm of Pd, i.e. 100% of metal, is fixed on the material of plant origin after the first pass. We can see that a single pass is enough to absorb all the palladium that is not desorbed after a second and even after a third pass.

Example 9

Ru, Ir, Ni are naturally present in a Pd-rich ore. Knowing how to selectively absorb Pd in the presence of these other elements can be very useful. The functionalized phenolic acids make it possible to obtain very good overall yields on a Pd, Ru, Ir mixture.

TABLE 22

Decontamination of Pd, Ru and Ir

| Initial conc. Pd mg/l | Final conc. Pd mg/l | Initial conc. Ru mg/l | Final conc. Ru mg/l | Initial conc. Ir mg/l | Final conc. Ir mg/l |
|---|---|---|---|---|---|
| 15 | 0 | 15 | 15 | 15 | 15 |

Example 10. Recycling Ni

Ni biosorption is an interesting and useful case. In addition, the toxicity of Ni implies total extraction if one wishes to be in agreement with the standards of the WHO relating to the quality of the drinking water or the standards of discharge, themselves very demanding for this element. This is why the functionalization of biosorbents has been studied.

The absorption is carried out with various chemically functionalized biosorbents (coffee grounds, hyacinth root powder, water lettuce root powder, pine cone powder, green algae for comparative purposes).

Procedure for the Biosorption of Ni in Batch:

1 g of functionalized biosorbent is added to the solution of $NiS_4.6H_2O$ (0.063 g/l). The mixture is stirred for 2 h and then filtered. The solid is dried at 85° C. overnight. The dry solid obtained is then heat-treated at 550° C. for 6 hours in order to obtain the ash enriched with nickel.

A) Ester functionalized coffee grounds autocatalysed with citric acid (form —COONa)
B) Autocatalyst functionalized hyacinth root powder with citric acid (form —COONa)
C) Non-functionalized green algae variable

TABLE 23

Ni concentration in the effluent

| Label | variable | Ni |
|---|---|---|
| Initial Ni conc. in the effluent | mg/l | 12 |
| Ni conc. in the effluent after contacting with A | mg/l | 0 |
| Ni conc. in the effluent after contacting with B | mg/l | 0 |
| Ni conc. in the effluent after contacting with C | mg/l | 3.73 |

The functionalization of the biomass leads to the formation of an effective biosorbent to remove traces of Ni in the solution if new carboxylic groups are introduced, in particular in COONa form. For comparison, we carried out the extraction with green algae. This biomaterial is chosen because it is rich in alginic acid which is known to complex nickel well thanks to the carboxylic group and may be compared with the biosorbents functionalized with citric acid. On the other hand, we observe the average efficiency of the algae due to the solubility of the alginic acids in the water which causes the passage of the complex in the filtrate. In addition, the mixture is difficult to filter. This result shows the advantage of phenolic acids whose carboxylate groups induce a high complexing potency at neutral pH and the carbonaceous structure renders the solid materials insoluble in water.

Study of the Different Parameters of Ni Biosorption

We have studied the maximum amount of Ni that can be extracted by the different biosorbents according to their mode of functionalization.

TABLE 24

Study of the different parameters of Ni biosorption

| Nature of biomass | Functionalization condition | m material | m material (form-COONa) | V (2M NaOH)/g of biomass | Fate functionalization (mol (NaOH)/g of biomasse) | Concentration of the metal solution | Biosorption capacity, mg/g of biomass | pH of the biomass after neutralization |
|---|---|---|---|---|---|---|---|---|
| Hyacinth root powder | Succinic anhydride + EtOH | 5 g | 4.3 g | 0.4 ml/g | 0.0008 mol/g | 40 mg/l | 29 mg/g | 7 |
| Hyacinth root powder | Succinic anhydride + EtOH | 5 g | 4.2 g | 0.72 ml/g | 0.0014 mol/g | 40 mg/l | 32 mg/g | 7 |
| Hyacinth root powder | Succinic anhydride + EtOH | 5 g | 4.2 g | 0.72 ml/g | 0.0014 mol/g | 1.024 g/l | 51 mg/g | 7 |
| Hyacinth root powder | Glutaric anhydride + AcOEt | 5 g | 3.4 g | 0.38 ml/g | 0.0007 mol/g | 40 mg/l | 28 mg/g | 7 |
| Coffee grounds | Succinic anhydride + EtOH | 5 g | 4.7 g | 0.16 l/g | 0.00064 mol/g | 40 mg/l | 22 mg/g | 7 |
| Coffee grounds | Succinic anhydride + EtOH | 5 g | 5.1 g | 0.28 ml/g | 0.0014 mol/g | 40 mg/l | 31 mg/g | 7 |

TABLE 24-continued

Study of the different parameters of Ni biosorption

| Nature of biomass | Functionalization condition | m material | m material (form-COONa)/g | V (2M NaOH)/g of biomass | Fate functionalization (mol (NaOH)/g of biomasse) | Concentration of the metal solution | Biosorption capacity, mg/g of biomass | pH of the biomass after neutralization |
|---|---|---|---|---|---|---|---|---|
| Coffee grounds | Succinic anhydride + EtOH | 5 g | 5.1 g | 0.28 ml/g | 0.0014 mol/g | 1.024 g/l | 33 mg/g | 7 |
| Pine cone | Succinic anhydride + EtOH | 5 g | 3.4 g | 0.2 ml/g | 0.0008 mol/g | 40 mg/l | 21 mg/g | 7 |
| Pine cone | Citric acid + EtOH | 5 g | 5.7 g | 0.88 ml/g | 0.0011 mol/g | 40 mg/l | 30 mg/g | 7 |
| Pine bark | Succinic anhydride + AcOEt | 5 g | 3.6 g | 0.7 ml/g | 0.0013 mol/g | 40 mg/l | 30 mg/g | 7 |
| Pine cone | Citric acid + EtOH | 5 g | 5 g | 0.8 ml/g | 0.0016 mol/g | 40 mg/l | 30 mg/g | 7 |
| Pine cone | Citric acid + $H_2O$ | 5 g | 5.8 g | 0.8 ml/g | 0.0017 mol/g | 40 mg/l | 25 mg/g | 10 |
| Coffee grounds | Citric acid + $H_2O$ | 5 g | 5 g | 0.8 ml/g | 0.0016 mol/g | 94 mg/l | 29 mg/g | 7 |
| Coffee grounds | Citric acid + EtOH | 5 g | 5 g | 0.9 ml/g | 0.0018 mol/g | 94 mg/l | 38 mg/g | 7 |

Five important parameters are highlighted: the carboxylate and non-carboxylic form, a neutral pH of biosorption, the agents and conditions of functionalization, the nature of the ecomaterials. The sodium carboxylate-rich biosorbents are very effective and can biosorb up to 55 mg of Ni per 1 g of biosorbent (case of hyacinth powder esterified with citritic acid in ethanolic medium).

Contrary to the works described in the literature (B. Zhu et al., J. Hazard, Mater 153 (2008) 300-308), the carboxylation with citric acid does not go through the formation of an intermediate anhydride and is not an oxidation reaction (Leyva-Ramos et al., Sep. Purif Tech 45 (2005) 41-49). A prior preparation of this anhydride leads to such a high degree of functionalization that the functionalized carbon skeleton becomes soluble in water during biosorption.

On the other hand, a self-catalyzed esterification reaction, without water, with a polycarboxylic acid whose first acidity has a pKa equal to or less than 4, or the use of a less rich anhydride in a carboxylic unit in a non-protic medium are efficient. Functionalization by succinic anhydride, maleic anhydride, phthalic anhydride, dicyclohexane dicarboxylic anhydride, in ethyl acetate leads to very similar results on the three types of biomass studied: hyacinth powder, coffee grounds and pine cones and pine bark To prove the generality of the nickel extraction method, we performed column biosorption filled with biomass, and no longer in batch.

Example 11: Extraction of Ni with Hyacinth Powder Functionalized with Citric Acid by a Column-Type Method Procedure for Column Biosorption:

10 g of biomass (hyacinth powder functionalized with citric acid) is put in the column. The synthetic effluent (10 l) containing 40 mg/l of Ni is passed twice in the column. The passage time of 10 L of solution is 45 min.

The initial Ni concentration in the effluent is 40 mg/l, after one pass it is 2 mg/l.

The complexation is still effective, 38 mg of Ni on the biomass is fixed. Only one pass is enough to absorb 95% Ni.

Example 12. Biosorption of Manganese

Plant derivatives rich in phenolic acids are good Mn biosorbents if properly functionalized. They can be used again in synthetic chemistry, especially in oxidation reactions.

Example 12.1 Synthetic Solution

Procedure for the Biosorption of $MnSO_4$:

1 g of hyacinth root powder functionalized with citric acid is added to 1 l of $MnSO_4$ solution (24 mg/l, at neutral pH). The mixture is stirred for 2 h and then filtered. The solid is dried in the oven at 85° C. overnight. The dry solid obtained is then heat-treated at 550° C. for 6 hours to obtain the ash enriched with manganese.

TABLE 25

Concentration in Mn

| Label | variable | Mn |
|---|---|---|
| Initial effluent | mg/l | 23.44 |
| Effluent after biosorption | mg/l | 0.4 |
| Ash | % weight | 18 |

The functionalized biosorbent is very effective in purifying the effluents loaded with manganese. By virtue of this method, we obtain manganese levels lower than those fixed by the regulations.

To verify the general interest of this result, it was implemented from industrial effluents resulting from the extraction of pyrite, i.e. with acidic media, rich in Mn, but of polymetallic composition.

Example 12.2 Industrial Effluent 1 g of material of plant origin was used for 1 l of effluent using two methods: batch and column. The results are equally effective despite the plurimetallic composition of the medium.

Example 24. Purification of the Neutral Industrial Effluent with the Functionalized Biomass (Hyacinth Powder Functionalized with Citric Acid/EtOH)

One liter of industrial effluent (pH=2.5-3.5) is neutralized with sodium hydroxide (2M NaOH) to a neutral pH, then eluted on a column containing 1 g of functionalized biomass (ground hyacinth powder functionalized with citric acid). After 1 pass at room temperature (30 minutes), the powder is dried at 85° C. The dry residue is calcined at 550° C. to obtain a powder enriched in metals.

We observe a partial decontamination of the effluent with 1 g of biomass per liter, because all the metallic elements are biosorbed. To obtain complete purification of the effluent, 8 g of functionalized biosorbent (hyacinth root powder functionalized by esterification autocatalysed with citric acid per liter of industrial effluent must be used.

TABLE 26

Purification of industrial effluents from the pyrite quarry

| | Esterified roots of water hyacinths | | Esterified pine trees | | Esterified coffee grounds | |
|---|---|---|---|---|---|---|
| | Initial conc. mg/L | Final conc. (1 Pass) mg/L | Initial conc. mg/L | Final conc. (1 Pass) mg/L | Initial conc. mg/L | Final conc. (1 Pass) mg/L |
| Al | 18.6 | 0 | 4.3 | 0 | 2.5 | 0 |
| Fe | 4.4 | 0.3 | 8.2 | 1 | 3.8 | 0.3 |
| Ca | 218 | 208 | 65.5 | 14 | 113 | 51.5 |
| Mg | 179 | 147 | 59 | 16 | 23 | 3.0 |
| Ni | 1.3 | 0 | 0.4 | 0 | 0 | 0 |
| Zn | 2.5 | 0 | 3 | 0 | 0.3 | 0 |
| Mn | 11.7 | 1.7 | 11.4 | 1.6 | 10 | 1.6 |

The purification of the effluent is very effective. Less than 1 ppm of Fe, Al and Mn remain after the first pass through the column. We can see that one pass is sufficient to effectively purify the industrial effluent. Unlike non-functionalized materials, all metal elements are retained (Al, Fe, Ni, Zn, Mn) but also Ca and Mg. This result is generalizable to the different types of functionalized materials. It may also be optimized easily by using 2 g of biomass per liter of effluent to be treated.

TABLE 27

Purification of neutral industrial effluent with functionalized biomass (hyacinth powder functionalized with citric acid)

| | Initial conc., mg/L | Pass 1, mg/L |
|---|---|---|
| Al | 3.1 | 0.4 |
| Ca | 58.2 | 29.6 |
| Fe | 1.9 | 0.5 |
| Mg | 37.8 | 27.6 |
| Mn | 9.1 | 0.8 |
| Na | 192.3 | 242.7 |

Example 13. Recycling Rare Earths

Growing importance and access to the resource are delicate geo-economic issues. The study of simple and effective recycling techniques is evident for various rare earths: Sc, Ce, Yb, Eu . . . .

Example 13.1. Extraction of Scandium with Hyacinth Powder Functionalized with Citric Acid Sc(NO$_3$)$_3$ hydrated (0.072 g) is solubilized in 1 l of water. It is very poorly retained by biosorbents such as water hyacinth roots. In contrast, Sc biosorbent capacities are improved after functionalization. The initial Sc concentration in the effluent is 26 ppm, after extraction it is 5 ppm.

The carboxylation of the biomaterial makes it possible to obtain an adsorption capacity of 21 mg/l from an initial concenration of 26 mg/l.

Example 13.2. Extraction of Scandium in the Presence of Excess of Ni with Hyacinth Powder Functionalized with Citric Acid Scandium is often extracted from other minerals from which it must be separated. This is for example the Ni.

Batch Procedure

To investigate the capacity of the citric acid functionalized biomass to selectively retain scandium over nickel, we prepared a synthetic effluent with concentrations of Sc=25 mg/l and Ni=72 mg/l, the separation being performed in batch.

We can see that the functionalized biomass selectively extracts scandium from nickel, even if the latter is in excess. Comparing the result with the extraction of nickel-free scandium, we can see that the biomass accumulates around 20 ppm of scandium which is comparable with the scandium/nickel mixture test, or 20 ppm of scandium have been fixed and the remaining complexant sites fixed nickel without replacing scandium with nickel.—

Column Procedure

To mimic the effluent purification transposition at the industrial level, we have considered purification on a column filled with carboxylated biomass. Knowing that the concentration of scandium in existing ores is very low, we prepared the solution of nickel and scandium with the ratio of 112 ppm of Ni to 2 ppm of Sc. The aim is to see if the scandium remains fixed on the column in the presence of a large excess of nickel which allows the biomass in scandium to be enriched after several passes of effluent with a low concentration of scandium.

0.6 g of biomass (hyacinth powder functionalized with citric acid) is put in the column. The synthetic effluent (0.6 ml) containing 112 mg/l Ni and 2.3 mg/l scandium is passed three times through the column. The residence time is 10 min.

TABLE 28

Ni and Sc concentrations

| | | Nickel, mg/L | Scandium, mg/L |
|---|---|---|---|
| Column procedure | Initial conc. | 112 | 2.3 |
| | Pass 1 | 68 | 0 |
| | Pass 2 | 64 | 0 |
| | Pass 3 | 64 | 0 |
| Batch procedure | Initial conc. | 72 | 25 |
| | Pass 1 | 51 | 4 |

The result obtained is spectacular: it shows a fast, simple, efficient and biobased method that purifies the industrial effluent charged with nickel and scandium and at the same time extracts scandium preferentially. This is a new method for enriching biomass in this rare and precious metal. It should be noted that scandium and nickel remain fixed on the biomass and are not eluted even after the third pass. So, only one column pass is enough. Passes 2 and 3 show that there is no desorption. Complexation with biomass is easily extensible to other rare earths such as Ce, Yb and Eu.

Example 13.3. Recycling of Ce

Complexation with biomass is easily extensible to other rare earths such as Ce. A solution of cerium at a concentration of 32 ppm was prepared. Extraction was performed with hyacinth root powder functionalized with citric acid. The concentration of cerium in the effluent before extraction with hyacinth powder functionalized with citric acid is 32 mg/l, after extraction it is 0.8 mg/l.

Virtually all cerium is complexed by the functionalized biomass.

Example 13.4. Recycling Ytterbium

The biosorption is studied with a catalytic solution of $Yb(NO_3)_3$ pentahydrate at 16 mg/l of ytterbium (Yb) and the results of this analysis are described below. The biosorbent used is the coffee grounds functionalized with citric acid. The concentration of ytterbium in the effluent before extraction with coffee grounds functionalized with citric acid is 16 mg/l, after extraction it is 1.0 mg/l.

The functionalized biomass is able to concentrate more than 15 mg of ytterbium.

Example 13.5. Recycling Europium

The biosorption is studied with a catalytic solution of $Eu(NO_3)_3$ hydrate at 13 mg/l of europium (Eu) and the results of this analysis are described below. The biosorbent used is the coffee grounds functionalized with citric acid. The concentration of europium in the effluent before extraction with coffee grounds functionalized with citric acid is 13 mg/l, after extraction it is 0 mg/l The entire europium of this concentration is biosorbed with the functionalized biomass.

Example 14. Recycling of Cu

The extraction was carried out with the coffee grounds functionalized with citric acid according to the ethanol method.

The biomass (citric acid/EtOH-functionalized coffee grounds) is put in a solution of $Cu(NO_3)_2 \cdot 3H_2O$ per 1 liter of solution. The suspension was stirred at room temperature, then filtered and the solid dried in an oven at 85° C.

Extraction of Copper with Coffee Grounds Functionalized with Citric Acid

TABLE 29

Recycling of Cu

| Biosorption period | Quantity of biomass/l | Initial conc. of Cu, mg/l | Final conc. of Cu, mg/l |
|---|---|---|---|
| 2 h | 1 g | 15 | 0 |
| 2 h | 1 g | 101 | 54 |
| 5 days | 2.5 g | 315 | 186 |

The data are superior to those in the literature: Int. J. Environ. Sci. Technol. (2013) 10: 611-622, Cerino-Cordova et al. 129 mg of copper were accumulated by the biomass in 5 days which shows a great capacity for extraction of the functionalized coffee grounds.

Example 15. Recycling of Co

Cobalt is a strategic element for two reasons: it is very useful in green technologies and could be exhausted between 22 years (increase of 10% of its consumption) and 57 years (current rate) compared to cost-effective resources. The possibility of recycling is therefore relevant. In addition, Co has been regulated by REACH as a carcinogen and problematic.

The materials of plant origin of the invention respond to this dual problem. Thus, for example, the extraction of $Co(NO_3)_2 \cdot 6H_2O$ with 1 g/l of hygrinth root powder modified with succinic anhydride in AcOEt makes it possible to recover 27 mg/l of Co.

Example 16. Recycling Pb

A lead solution was prepared from $Pb(NO_3)_2$. The extraction was carried out with the coffee grounds functionalized with citric acid/EtOH.

Extraction of Lead with Coffee Grounds Functionalized with Citric Acid

TABLE 30

Extraction of lead with coffee marks functionalized with citric acid

| Biosorption period | Quantity of biomass/l | Initial conc. of Pb, mg/l | Final conc. of Pb, mg/l |
|---|---|---|---|
| 2 h | 1 g | 15 | 0 |
| 2 h | 1 g | 142 | 86 |
| 5 days | 1.25 g | 213 | 46 |

The data are superior to those in the literature: Int. J. Environ. Sci. Technol. (2013) 10: 611-622, Cerino-Cordova et al.

1 g of biomass extracts 56 mg of lead in 2 hours. 170 mg of lead were accumulated by 1.25 g biomass in 5 days, which shows a high extraction capacity of lead with functionalized coffee grounds.

Example 17. Recycling of Cd

A solution of cadmium at a concentration of 15 ppm was prepared from $Cd(NO_3)_2 \cdot 4H_2O$. The extraction was carried out with 1 g of coffee grounds functionalized with citric acid/EtOH. The concentration of cadmium in the effluent before extraction with coffee grounds functionalized with citric acid/EtOH is 15 mg/l, after extraction it is 0 mg/l.

All of the cadmium is absorbed by 1 g of biomass in 2 hours.

The following examples show the organic synthesis reactions implemented according to the method of the invention.

Example 15. Coupling Reactions with Materials Having Fixed Pd

Recycled catalytic systems are called Phyto-Pd.

Preparation Procedure for Material Having Fixed Pd (Phyto-Pd):

23.4 mg of ash (coffee grounds) enriched in palladium (54% of palladium) are diluted in 3.25 mL of 6N HCl acid and refluxed for 6 hours. After returning to ambient temperature, filtration and concentration under reduced pressure, 44 mg of a hygroscopic orange-brown powder is obtained (20.5% of palladium).

Example 15.1

Coupling reaction between brominated heterocyclic derivatives with boronic acids (Suzuki reaction). The Suzuki reaction reaction may be in water, butanol or a mixture of water/glycerol or butanol/glycerol.

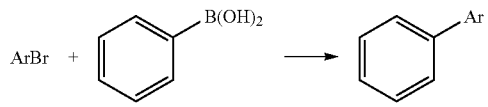

particular phosphine: ((t-Bu)$_2$PhPH)BF$_4$, a liganded Pd: Pd (0.12 mol %), the reaction lasts 13 hours and the catalyst is not recyclable. Finally, the yield is lower (86%).

General Experimental Protocol for Suzuki Reaction

The aryl halide (1.25 mmol, 1 equiv), phenyl boronic acid (1.3 mmol, 1.1 equiv), potassium carbonate (1.5 mmol, 1.2 equiv) and 0.1 mol % of Pd-based catalyst (Phyto-Pd) are put in a flask. 2.5 ml of solvent is added and the suspension obtained is put under argon. The reaction mixture is stirred at 95° C. for 2 h. After 2 hours the mixture is cooled. The product is extracted with ethyl acetate and washed with water. Conversion is determined by GC/MS with dodecane as an internal standard.

TABLE 31

Results of coupling reactions

| Boronic acid | Bromide of heteroaryls or aryls | Biosorbant used | T(h) | Solvent | Conversion |
|---|---|---|---|---|---|
| PhB(OH)$_2$ | 2-bromothiophene | Hyacinth root powder | 2 | Glycerol | 92% |
| PhB(OH)$_2$ | 2-bromothiophene | Hyacinth root powder | 2 | nBuOH | 73% |
| PhB(OH)$_2$ | 2-bromothiophene | Hyacinth root powder | 2 | H$_2$O/nBuOH (9/1) | 85% |
| PhB(OH)$_2$ | 3-bromopyridine | Lignine | 2 | H$_2$O | 75% |
| PhB(OH)$_2$ | 3-bromopyridine | Hyacinth root powder | 2 | H$_2$O | >99% |
| PhB(OH)$_2$ | 2,5-dibromothiophene | Hyacinth root powder | 2 | nBuOH | 39% (monocoupling = 56% dicoupling = 44%) |
| 3,4-dichlorophenylB(OH)$_2$ | N-(4-fluoro-2-bromophenyl)acetamide | Hyacinth root powder | 2 | Glycerol/ nBuOH | >99% |

The last example of the table above is noteworthy, since it corresponds to the synthesis of a key intermediate of the bixafen. The reaction is quantitative in two hours, without addition of ligand, phosphine or particular additive. The catalyst is recyclable at the end of the reaction. Pd is reduced in situ to black Pd by glycerol. It is isolated by filtration, introduced into a 1M nitric acid solution. Functionalized hyacinth powder allows quantitative recovery of Pd in two hours and regeneration of Phyto-Pd by the heat treatment/activation sequence with HCl. The coffee grounds are just as effective. These results may be advantageously compared with those described in the literature (WO 2015/011032 A1, PCT/EP2014/065463) where the method requires a very Entry 1 was carried out on a scale of 20.4 g of 2-bromothiophene, i.e. 111 mg of Phyto-Pd (0.125 mmol of Pd). This is an interesting case of homogeneous catalysis, Phyto-Pd is entirely soluble in the coupling solvent. The catalyst was recycled and reused from the catalytic system in the same reaction. The procedure is based on the filtration of the Pd formed at the end of the reaction and placed in the aqueous phase at pH=2.5 with nitric acid. After stirring for 2 hours, the results obtained are spectacular: 84% of Pd is re-extracted by the root powder of water hyacinths. After transformation of the root extracts according to the standard method, the catalytic activity of the regenerated Phyto-Pd is preserved.

TABLE 32

Mineral composition of solids and solutions invoked in palladium recycling (MP-AES analyzes (% mass for solids, mg/l for liquid phases).

| | Pd |
|---|---|
| Liquid phases (mg/l) | |
| Aqueous phase resulting from reaction | 0 |
| Organic phase resulting from reaction | 0 |
| Effluent before biosorption | 13.2 |
| Effluent after biosorption | 0.01 |
| Solid phase (% weight) | |
| Phyto-Pd | 13.8 |

The method is generalizable to other heterocyclic halogenated derivatives in glycerol.

It is also possible to carry out conversions with butanol in the case of nonhydrophilic brominated derivatives (bromothiophene) or in water with nitrogenous heterocycles (bromopyridine). The yields are comparable. These reactions are therefore remarkably efficient, simple to implement and economical (no ligand, no additive) and totally eco-compatible (green solvents and recyclability of Phyto-Pd.

Likewise, these catalysts can promote couplings between boronic acids and heterocyclic brominated derivatives. Again, no ligand is needed. Green solvents lead to very good yields.

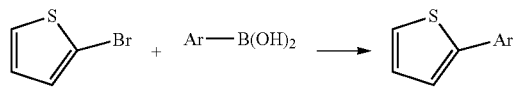

TABLE 33

Reactions with boronic acids

| Boronic acid | T (h) | Conversion (%) |
|---|---|---|
| 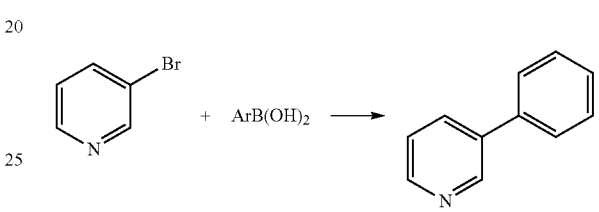 4-MeO-C6H4-B(OH)2 | 4 | 88 |
| 2-thiophene-B(OH)2 | 50 | 95 (84) |
| 5-indole-B(OH)2 | 4 | >99 (90) |
| 4-Cl-C6H4-B(OH)2 | 4 | 94 |

TABLE 33-continued

Reactions with boronic acids

| Boronic acid | T (h) | Conversion (%) |
|---|---|---|
| 3,4-diCl-C6H3-B(OH)2 | 4 | 99 |

It is thus possible to couple two thiophenes together, which opens access to conductive compounds.

The Suzuki heterocyclic series reaction may also be carried out using Phyto-Pd recycled by biosorption with coffee grounds. The reaction is carried out in water with a yield of 97%.

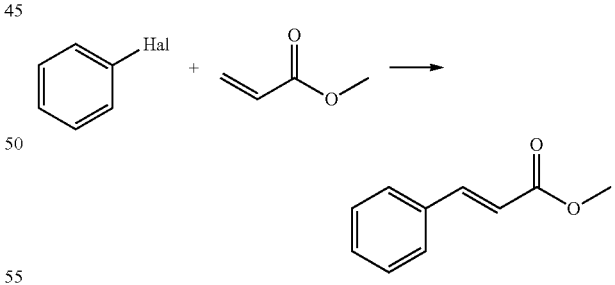

Experimental Protocol for Suzuki's Reaction in Water 3-bromopyridine (4.75 mmol, 1 equiv), phenyl boronic acid (5.23 mmol, 1.1 equiv), potassium carbonate (5.7 mmol, 1.2 equiv), and 1 mol % of Pd base catalyst (20.1% by weight of Pd in the catalyst) is put in a flask. 9.5 ml of solvent is added and the suspension obtained is put under argon. The reaction mixture is stirred at 95° C. for 2 h. After 2 hours the mixture is cooled. The product is extracted with ethyl acetate and washed with water. The conversion of 97% is determined in GC/MS with dodecane as an internal standard.

Example 15.2 Reaction of Iodobenzene with Methyl Acrylate (Heck Reaction)

Iodobenzene (1.4 mmol, 1.4 equiv), potassium carbonate (1.3 mmol, 1.3 equiv), 0.5 mol % of Phyto-Pd catalyst (19% mass of Pd in the catalyst) and methyl acrylate (1 mmol, 1 equiv) are dissolved in gamma-valerolactone (2 ml) under argon at room temperature. The reaction mixture is heated to 120° C. for 4 h. After 4 hours, the reaction is cooled and analyzed by GC/MS with dodecane as an internal standard. The conversion is total. 93% of monoadduit are observed and 7% of diadduit.

The reaction is compared with commercial catalysts such as PdCl2 and Pd(OAc)$_2$. The conversion is total in both cases, but the ratio between the monoadduit and the diadduit is 80/20 and 87/13 respectively. This difference shows that the reaction with Phyto-Pd is more selective with respect to the monocoupling product.

Using bromobenzene, only monoadduct is observed.

Another Heck reaction, below, demonstrates a much higher conversion percentage with the biobased catalyst relative to the commercial catalyst.

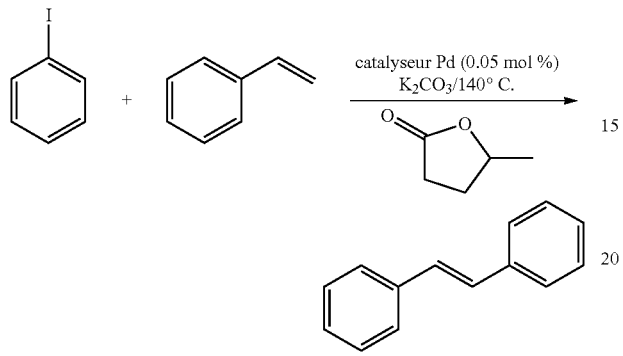

TABLE 34

| | Results | |
|---|---|---|
| Catalyst | Time | Conversion % |
| Phyto-Pd | 15 mn | 74 |
| K$_2$PdCl$_4$ | 15 mn | 53 |
| Phyto-Pd | 30 mn | 96 |
| K$_2$PdCl$_4$ | 30 mn | 82 |

Example 15.3: Sonogashira Reaction

With recycled Phyto-Pd, Sonogashira coupling may be performed without ligand and without copper salts. The industrial example of coupling butyn-3-ol and 4'-hydroxy-3'-iodo-biphenyl-4-carbonitrile illustrates the potential of Phyto-Pd in this type of reaction.

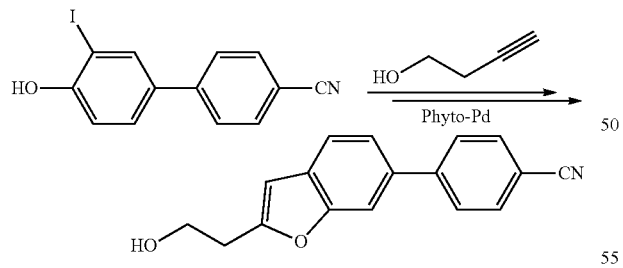

In 100 ml of a 50/50 glyecrol/butanol mixture, 0.05 mol of iodinated derivative, 0.1 mol of butyn-3-ol are added in the presence of 0.1 mol of K$_2$CO$_3$ and of derived Phyto-Pd. water lettuce (0.5 mol % Pd). The reaction medium is heated to 100° C. After 4 hours, the reaction is cooled and analyzed by GC/MS with dodecane as an internal standard. The conversion is total.

This result is particularly interesting because it is a key step in the industrial synthesis of ABT-239, a histamine H3 receptor antagonist. It may be advantageously compared with data in the literature describing ligated palladium catalysts (example: PdCl$_2$(PPh$_3$)$_2$) complex) in the presence of copper salts (CuI): Organic Method ReEASrch Development 2005, 9 (1), 45-50), which further requires higher amounts of Pd (1 mol % in the previous reference).

The Sonogashira reaction catalyzed by Phyto-Pd may be extended to the synthesis of π-conjugated polymers, such as polyarylenes, polyphenylacetylenes. Again, copper salts and the introduction of ligands is not useful. This is a simple and effective access to polymers used in OLEDs.

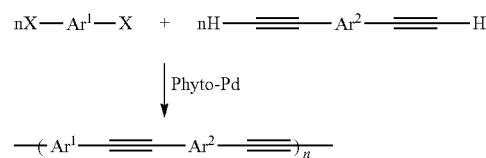

Example: X=I, Ar$^1$=Ar$^2$=Ph

In 100 ml of a 50/50 glycerol/butanol mixture, 0.1 mol of 1,4-diiodobenzene, 0.1 mol of 1,4-diethynylbenzene are added in the presence of 0.1 mol of K$_2$CO$_3$, and Phyto-Pd derived from the pine cone (0.5 mol % Pd). The reaction medium is heated to 100° C. After 8 h, the reaction is cooled and analyzed by NMR and IR showing the formation of polycondensation products. With phenylacetylene, the conversion is complete after 2 hours of reaction. This result is advantageously compared with that of Yang (J. Org Chem 2005, 70, 391-393) which expects 80% of yield after 24 hours and 1% of Pd.

Example 15.4: Reductive Chemistry of Pd(II)

Example 15.4.1: Reduction of an Enone with the Ashes of Phyto-Pd

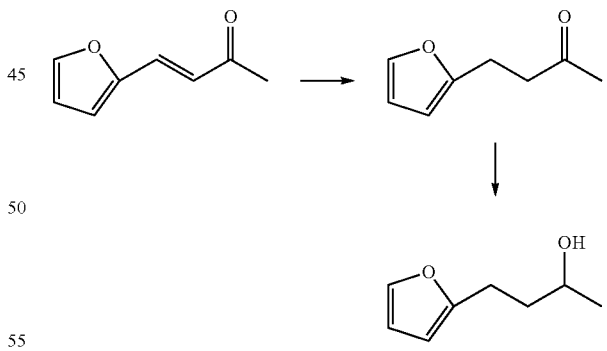

Enone (2.5 mmol, 1 equiv.) and Phyto-Pd (from controlled heat treatment of water hyacinth roots) (0.15 equiv.) are suspended under argon in degassed THF (2 ml). Formic acid (5.0 mmol, 2 equiv) is added and the resulting mixture is refluxed. After 3 hours, the mixture is filtered on dicalite and concentrated under reduced pressure. A yield of 85% is obtained in ketone. It is important to note that the reaction is inoperative with Pd oxide. By tightening the conditions (time, catalytic charge), the percentage of alcohol becomes the majority.

Example 15.4.2 Isomerization of an Exocyclic Double Bond of 2-Cyclopentenone

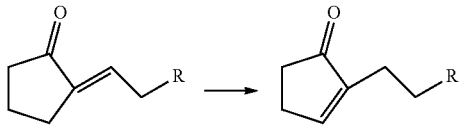

R=alkyl, H

The cyclopentenone (1 mmol, 1 equiv) is added to 0.1 mol % of Phyto-Pd catalyst (20% by weight of Pd in the catalyst), then the mixture obtained is stirred for 16 hours under argon at room temperature. The reaction mixture becomes dark black. After stirring overnight, the composition of the reaction mixture is analyzed by GC/MS. The conversion to product bearing an endocyclic double bond is 52%.

Example 16: Bio-Sourced Chemistry of Iron (Fe)

Procedure for Preparing the Material Having Fixed Iron (Phyto-Fe):

400 mg of ash (hyacinth root powder) enriched with iron (2% iron) is diluted in 55.5 mL of 6N HCl. The mixture is refluxed for 6 hours. After returning to ambient temperature, filtration and concentration under reduced pressure, 430 mg of a hygroscopic yellow powder are obtained (1.3% iron).

Example 16.1: General Protocol for the Oxidation of Benzyl Alcohol to Aldehyde with Phyto-Fe without Ligand Phyto-Fe (20 mmol, 2 mol %) is added in 1 ml of $H_2O$ and stirred for 20 min to obtain a clear yellow solution. After addition of the benzyl alcohol (1 mmol) the reaction mixture is stirred vigorously, then the $H_2O_2$ (30% in water, 2 mmol, 0.2 ml) is added dropwise in 10 min using a syringe pump at room temperature. The reaction mixture is stirred for 3 h, then the aldehyde is extracted with ethyl acetate and analyzed GC/MS with dodecane as internal standard. A yield of 35% is obtained.

Example 16.2: General Protocol for Oxidation of Benzyl Alcohol to the Aldehyde with Phyto-Fe Activated by a Diazotized Ligand Phyto-Fe (20 mmol, 2 mol %) and the ligand (20 mmol, 2 mol %, for example phytophytine) are added in 1 ml of $H_2O$. The mixture is stirred for 20 minutes to obtain a clear yellow solution. After the addition of the benzyl alcohol (1 mmol) in the solution, the reaction mixture is stirred vigorously and $H_2O_2$ (30% in water, 2 mmol, 0.2 ml) is added dropwise over 10 min using a syringe pump at room temperature. The reaction mixture was stirred for 3 h, then the aldehyde was extracted with ethyl acetate and analyzed in GC/MS with dodecane as the internal standard. A yield of 59% is obtained.

An innovative recovery of the iron was carried out with the biomaterial richest in Fe.

TABLE 35

| | Metal contents | | | | | | | |
|---|---|---|---|---|---|---|---|---|
| Label | Al | Ca | Fe | K | Mg | Mn | Na | Zn |
| Root powder of hyacinths ppm | 24626 | 56187 | 5560 | 94899 | 37871 | 2343 | 68848 | 1451 |
| % weight | 2.46 | 5.62 | 5.57 | 9.49 | 3.79 | 0.23 | 6.88 | 0.15 |

The root extracts were heat-treated at 550° C. and then activated with 6N HCl at reflux for 6H. After concentration of the reaction medium, the yellow solid obtained, called Phyto-Fe, was tested in unusual reactions of EASr.

Example 16.3. Oxidative Halogenation and Unusual EASr (Nitration, Thiocyanation)

Phyto-Fe comprising 0.05 mol of iron, in the presence of an equimolar amount of sodium bromide (or potassium) and anisole are heated at 80° C. overnight in the presence of 200 mg of montmorillonite K10.

The monobromation product is obtained with a yield of 74%. This result is remarkable because bromination is possible without bromine. It is particularly surprising, because from a thermodynamic point of view, Fe(III) is not sufficiently oxidizing to oxidize a bromide to dibrome. It should also be noted that the solid support is not silica, but montmorillonite, which does not pose the same problems of toxicity.

This method of bromination is unique if one refers to data from the literature. The table presented below highlights the advantage of the technology presented: it is based on the use of a non-noble catalyst, easy to access, without dangerous co-oxidant, without solvent, without silica and with a direct and very easy to implement method, and using bio-sourced and sustainable materials. Conventional methods require dibroma (irritant) in the presence of Lewis acids or NBS, which generates a toxic imide. The examples given below are based on the use of NaBr in the presence of complex catalysts or compounds of noble metals, oxidants and toxic solvents. A comparative literature review proves that the proposed method is a real advance in the field of Journal of Organic Chemistry, 67 (13), 4487-4493, 2002; Eur. Pat. Appl. 1138657, 2001; Tetrahedron Letters, 31 (14), 2007-10, 1990; Eur. Pat. Appl., 1138657, 2001; Bulletin of the Korean Chemical Society, 23 (5), 773-775, 2002; Synthetic communications, 31 (19), 2995-2963, 2001; Journal of Chemical ReEASrch, (6), 366-368, 2006; Huaxue Yu Shengwu Gongcheng, 29 (11), 47-49, 2012; Catalysis Science & Technology, 5 (10), 4778-4789, 2015; Journal of Molecular Catalaysis A: Chemical, 371, 56-62, 2013; Chemical, 371, 56-62, 2013 ChemSusChem 6 (8) 1337-1340, 2013; Catalysis Letters, 137 (3-4), 190-201, 2010; Green Chemistry, 8 (10), 916-922, 2006; Synthetic communications, 28 (8), 1463-1470, 1998; Synthesis (2), 221-223, 2006; Tetrahedron letters, 44 (49), 8781-8785, 2003; e-EROS Encycl. of Reagents for Organic Synthesis 1-9, 2006; Advanced Synthesis & Catalysis, 351 (11+12), 1925-1932, 2009).

It should be noted that it is possible to extend the concept to chlorination reactions, but especially to aromatic series iodization. Thus, for example, the method allows tri-iodination of aniline or iodination of anisole or thiophene.

The aromatic derivative (0.1 mmol, 1 eq), Phyto-Fe (0.105 g (5.3% iron, 0.1 mmol, 1 eq), NaI (0.1 mmol, 1 eq) and montmorillonite K10 (0.2 g) are mixed and stirred at 80° C. for 24 hours. At the end of the reaction, the mixture is cooled to room temperature, washed with dichloromethane and analyzed in GC-MS, then in NMR.

TABLE 36

| Label | Conv % |
| --- | --- |
| Anisole | 65% |
| Thiophène | 64% |

The method may also be extended to other salts, such as KSCN, $KNO_3$, and thus allow thiocyanation or direct nitration under very mild conditions.

TABLE 37

| Label | Conv % |
| --- | --- |
| KSCN | 61% |
| $KNO_3$ | 83% (79% yield) |

Example 17. Bio-Sourced Zinc (Zn) Chemistry

Phyto-Zn is prepared by adding 1 gram of water hyacinth root extract in 100 mL of 10 mg/l Zn solution. After stirring for 2 h, the powder is filtered, dried and treated at 550° C.

Example 17.1: Condensation Reaction of a Carbanion on a Carbonyl Compound (Doebner-Knoevenagel Type Reaction)

Phyto-Zn recovered by recycling has interesting Lewis acid properties. The formation of C—C bonds by Doebner-Knoevenagel type reaction is an interesting example. It is involved in the synthesis of many compounds of interest such as atorvastatin, the active ingredient of a Pfizer anticholesterol drug known as Tahor in France or Lipitor in the United States, or imiquimod, principle active ingredients of Aldara and Zyclara, immune-modifying drugs used to treat skin conditions. Typical reaction conditions involve the use of solvents and a base in stoichiometric amount.

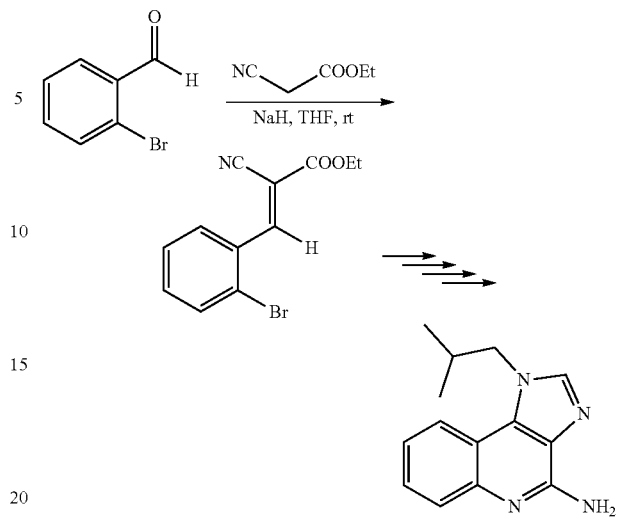

Synthesis of Imiquimod

The use of green solvents or the absence of solvent and the use of heterogeneous catalysis are two possible ways to make this reaction greener. The catalytic activity of zinc chloride, Lewis acid catalyst, in the absence of solvent has been demonstrated for the Knoevenagel reaction. However, zinc chloride is a very hygroscopic compound, difficult to handle and this is homogeneous catalysis.

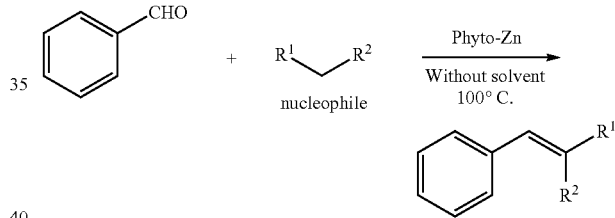

TABLE 38

| Catalyst | Malononitrile | Methyl cyanoacetate | Acetylacetone | Ethyl acetoacetate |
| --- | --- | --- | --- | --- |
| — | 0% | 0% | 0% | 0% |
| Phyto-Zn | 97% | 33% | 51% | 53% |
| $K_2ZnCl_4$ | 82% | 44% | <5% | 0% |

These results prove the interest of this recycling technique. It leads to a Phyto-Zn whose activity is at least equal to or greater than $K_2ZnCl_4$, the zinc salt present in Phyto-Zn.

Experimental Protocol for the Knoevenagel Reaction

In a reactor, Phyto-Zn (0.06 g, 5 mol % Zn), previously thermally treated for 5 min at 150° C., is introduced with benzaldehyde (5 mmol, 1 equiv.) and malononitrile (5 mmol, 1 equiv.) at room temperature. The reaction mixture is then heated at 100° C. for 1 hour. The solution is cooled and the product formed is extracted with ethyl acetate. The conversion is established by GC/MS with biphenyl as an internal standard. It is 97% Knoevenagel adducts.

Example 18. Bio-Sourced Chemistry of Nickel (Ni)

The Ni-loaded biosorbent is useful in organic synthesis. For example, it is a good coupling reaction catalyst, such as the Suzuki reaction.

Procedure of the Suzuki Reaction 5 g of ash derived from water hyacinths functionalized and treated at 550° C. are diluted in 15 ml of formic acid. The solution is refluxed. The solution gradually turns from black to green, reflecting the formation of nickel formate. After 7 h, the mixture is cooled and filtered, the solid is washed with formic acid and then with water. It is redissolved in hot hot water and the medium is evaporated under reduced pressure. It is dried and then engaged in Suzuki's reaction.

The eco-formate of Ni is dissolved in a glycerol/BuOH mixture (1/1 by volume) in the presence of two equivalents of potassium carbonate, 1.2 equivalents of boronic acid and one equivalent of iodobenzene. The mixture is heated to 120° C. for 8 hours. 80% of coupling product is then observed by MS GC analysis with respect to the internal reference (dodecane).

Example 19. Bio-Sourced Chemistry of Rare Earths

The powder filled with cerium was calcined and recovered in the reaction of Biginelli.

Procedure for Preparing Phyto-Ce:

45 mg of ash (citric acid-modified hyacinth root powder) enriched with cerium is diluted in 6.25 ml of 6N HCl; the medium is refluxed for 6 hours. After returning to ambient temperature, filtration and concentration under reduced pressure, 42 mg of a hygroscopic yellow powder is obtained (26% cerium).

Procedure of the Biginelli Reaction:

The solution of ethyl acetoacetate (0.013 g, 0.1 mol), 4-methoxybenzaldehyde (0.014 g, 0.1 mmol) and urea (0.018 g, 0.3 mol) in ethanol (0.05 g) ml) is refluxed in the presence of Phyto-Ce (0.037 g, 0.025 mol) for 2.5 hours. Part of the solution is removed, centrifuged and the liquid is passed into the GCMS. The 93% conversion is observed after 2.5 hours.

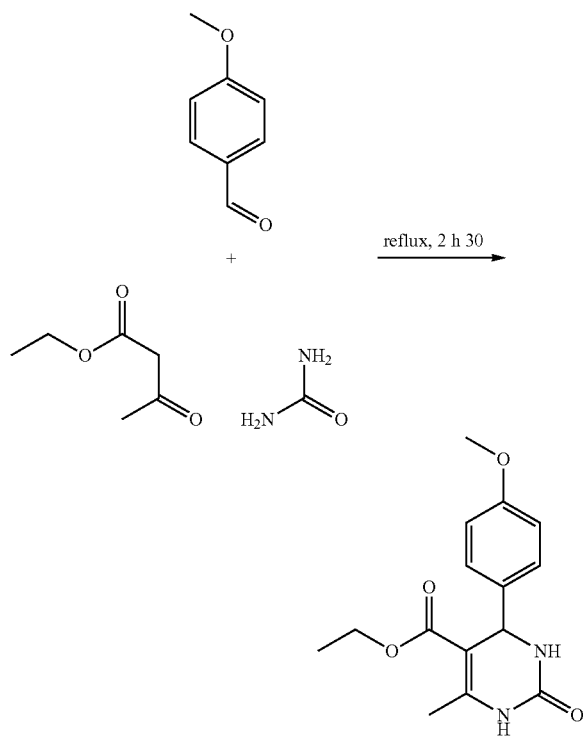

Reaction of Biginelli with a Phyto-Ce

Example 20. Epoxidation with Ashes Derived from Mn Extraction Using Water Hyacinth Root Powder The epoxidation of the alkenes may also easily be carried out from the ashes resulting from the extraction of Mn using the water hyacinth root powder in the presence of a co-oxidant such as hydrogen peroxide. The method may be advantageously compared to the methods of the literature. The method is simple since it is a direct recovery of ashes. No activation has been performed.

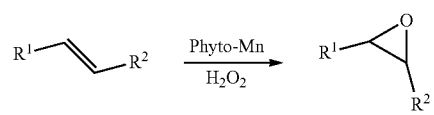

TABLE 39

| Substrate | Phyto-Mn: Ash | Phyto-Mn: EcoMn |
|---|---|---|
| Styrene | 100% | 91% |
| Limonene | 79% | 50% |
|  | (of which 93% di-epoxyde) | (100% of monoepoxyde) |

The easy obtaining of the limonene di-epoxide is very interesting because it is a molecule that can replace epichlorohydrin, without having the disadvantages of its toxicity.

General Procedure:

NaHCO$_3$ (1.5 g, 18 mmol, 5 eq), the Mn-enriched ashes derived from the water hyacinth root powder (0.071 g, 0.02 mmol, 0.005 eq Mn, Mn in the ash=1 79%), the DMF/H$_2$O mixture (1/1) (3.3 ml) and styrene (0.413 ml, 3.6 mmol, 1 eq) are added to a 25 ml flask at 30° C. in air. After stirring for 10 minutes, 30% H$_2$O$_2$ (3.3 ml, 36 mmol, 10 eq) is added dropwise over 2 hours to the reaction mixture at 30° C. in air. Stirring is continued for another 30 minutes and then the reaction is cooled to room temperature. The product is extracted with dichloromethane and analyzed by GC MS.

The invention claimed is:

1. Method for preparing a material of plant origin rich in phenolic acids, comprising at least one metal, said method comprising the following steps:
   a. preparation of a material of plant origin from a dead plant chosen from:
      aquatic plants;
      materials rich in tannins;
      materials rich in lignin; and
      obtaining a material of plant origin, rich in phenolic acids, in which the ratio of the intensity of the vibration band of the C=O bond of the COOH group and the intensity of each of the vibration bands the aromatic ring determined in FT-IR is between 0.5 and 4;
   b. bringing into contact the material of plant origin obtained at the end of step a) with an effluent comprising from 0.1 to 1000 mg/l of at least one metal; and
   c. obtaining a material of plant origin rich in phenolic acids comprising from 1 to 30% by weight of at least one metal relative to the total weight of the material.

2. Method for the decontamination or treatment of an effluent comprising at least one metal, said method comprising the following steps:

a. preparation of a material of plant origin from a dead plant chosen from:
   aquatic plants;
   materials rich in tannins;
   materials rich in lignin; and
   obtaining a material of plant origin, rich in phenolic acids, in which the ratio of the intensity of the vibration band of the C=O bond of the COOH group and the intensity of each of the bands of the aromatic ring vibration determined in FT-IR is between 0.5 and 4;
b. bringing into contact the material of plant origin obtained at the end of step a) with an effluent comprising from 0.1 to 1000 mg/l of at least one metal, and
c. obtaining an effluent comprising less than 100 mg/l by weight of said at least one metal.

3. Method according to claim 1 wherein the material of plant origin is chosen from:
   the roots of aquatic plants;
   coffee grounds or tea grounds;
   wheat straw, pine cones, pine bark, coconut husks.

4. Method according to claim 1, wherein the material of plant origin comprises phenolic acid functions and is capable of fixing more than 90% by weight, of at least one metal included in an effluent, said effluent comprising from 0.1 to 1000 mg/l of at least one metal.

5. Method according to claim 1 wherein the metal compound comprises at least one metal selected from platinoids, rare earths; or from the group consisting of Zn, Mn, Ni, Cu, Fe, Al, Ca, Mg, As, Sb, Cr, Cd, Ni and Co.

6. Method of claim 1 wherein:
   when the material of plant origin is water hyacinth, the effluent comprises at least one metal selected from Sc, Ni, Ce, Yb, Co, Ni, Cu, Pd, Pt, Rh, Mn, Fe, Zn, As, Cr or Sb;
   when the material of plant origin is water lettuce, the effluent comprises at least one metal chosen from Pd, Pt, Rh or Ni;
   when the material of plant origin is coffee grounds, the effluent comprises at least one metal chosen from Pd, Pt, Rh, Mn, Fe, Zn, Ni or Cd.

7. Method according to claim 1, wherein the material of plant origin has a ratio of the intensity of the absorption band of the C=O bond of the COOH group and of the absorption band of the aromatic ring determined in FT-IR less than 1.

8. Method according to claim 7 comprising a step of functionalizing the material of plant origin obtained at the end of step a), said step being prior to step b), and obtaining a source material in which the ratio of the intensity of the absorption band of the C=O bond of the COOH group and of the aromatic ring absorption band determined in FT-IR is greater than 1.

9. Method according to claim 8 wherein the functionalization step is performed via:
   a carboxylation reaction of the material of plant origin obtained at the end of step a) with a carboxylic acid anhydride in an aprotic polar solvent; or
   a autocatalysed esterification reaction between the material of plant origin obtained at the end of step a) and a polyacid, this reaction taking place in a solvent; or
   an esterification reaction followed by hydrolysis and transfunctionalization.

10. Material of plant origin, rich in phenolic acids, comprising at least one metal, said material being obtained according to the method of claim 8, further comprising functionalized phenolic acid functional groups.

11. Material of plant origin, rich in phenolic acids, comprising at least one metal, said material being obtained according to the method of claim 1.

12. Material according to claim 10, wherein the functionalization rate of the material of plant origin is between 0.0007 and 0.0014 $mol_{NaOH}$/g of material in the case of water hyacinth and between 0.0006 and 0.0018 $mol_{NaOH}$/g of material in the case of coffee grounds.

13. Method for implementing an organic synthesis reaction comprising the following steps:
   a. heat treatment of a material according to claim 11, and obtaining a calcined material;
   b. implementation of an organic synthesis reaction involving the calcined material as a catalyst.

14. Method according claim 13, wherein step a) comprises an acidic treatment of the calcined material.

15. Method according to claim 13 wherein the organic synthesis reaction is selected from:
   the coupling reactions,
   the reduction reactions,
   the isomerization reaction of an exocyclic double bond;
   the oxidation reactions;
   oxidative halogenation reactions;
   electrophilic substitution reactions;
   condensation reactions;
   multi-component reactions; and
   oxidation reactions of alkenes.

16. The method of claim 1, wherein the step of bringing into contact the material of plant origin obtained at the end of step a) with an effluent comprising from 0.1 to 1000 mg/l of at least one metal, is performed for a duration of between 1 hour and 2 hours, at a temperature between 10 and 30° C.

17. Method according to claim 1, wherein the material of plant origin comprises phenolic acid functions and is capable of fixing more than 99% by weight, of at least one metal included in an effluent, said effluent comprising from 0.1 to 1000 mg/l of at least one metal.

18. Method of claim 1 wherein:
   when the material of plant origin is water hyacinth, the effluent comprises at least one metal selected from Sc, Ni, Ce, Yb, Co, Ni, Cu, Pd, Pt, Mn, Fe, Zn or As;
   when the material of plant origin is water lettuce, the effluent comprises at least one metal chosen from Pd, Pt or Ni;
   when the material of plant origin is coffee grounds, the effluent comprises at least one metal chosen from Pd, Pt, Mn, Fe, Zn, Ni or Cd.

19. Material of plant origin, rich in phenolic acids, comprising at least one metal, wherein the material is dehydrated, and said plant origin being chosen from:
   materials rich in tannins;
   materials rich in lignin,
   said material having a ratio of the intensity of the absorption band of the C=O bond of the COOH group and the aromatic ring absorption band determined in FT-IR is greater than 1 and possibly comprising phenolic acid functions functionalized.

20. Material of plant origin, rich in phenolic acids, comprising at least one metal, said material being obtained according to the method of claim 2.

* * * * *